US007666391B2

(12) United States Patent
Ruoslahti et al.

(10) Patent No.: US 7,666,391 B2
(45) Date of Patent: Feb. 23, 2010

(54) BREAST HOMING PEPTIDES AND METHODS OF IDENTIFYING SAME USING AMINOPEPTIDASE P

(75) Inventors: Erkki Ruoslahti, Rancho Santa Fe, CA (US); Markus Essler, La Jolla, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 435 days.

(21) Appl. No.: 10/158,566

(22) Filed: May 29, 2002

(65) Prior Publication Data

US 2003/0232762 A1 Dec. 18, 2003

Related U.S. Application Data

(60) Provisional application No. 60/453,687, filed on Jun. 1, 2001.

(51) Int. Cl.
*A61K 49/00* (2006.01)
*A01N 37/18* (2006.01)
(52) U.S. Cl. .......................................... 424/9.1; 514/2
(58) Field of Classification Search ................. None
See application file for complete search history.

(56) References Cited

U.S. PATENT DOCUMENTS

| 5,622,699 A | 4/1997 | Ruoslahti et al. .......... 424/93.6 |
| 5,641,497 A | 6/1997 | Bevins et al. ............... 424/405 |

FOREIGN PATENT DOCUMENTS

| EP | 0478 101 | 4/1992 |
| WO | WO 93/22338 | 11/1993 |
| WO | WO 98/10795 | 3/1998 |
| WO | WO 99/46284 | 9/1999 |

OTHER PUBLICATIONS

Jain, Scientific American, Jul. 1994, 58-65.*
Bowie, et al. Science, vol. 247: 1306-1310, 1990.*
Lazar, et al. Mol. Cell. Biol., 8(3): 1247-1252, 1988.*
Burgess, et al. J. Cell Biol. 111: 2129-2138, 1990.*
Ngo et al., in "The Protein Folding Problem and Tediary Structure Prediction", 1994, Merz, et al. (ed.), Birkhauser, Boston, MA, pp. 433, and 492-495.*
Skolnick et al., From genes to protein structure an function: novel applications of computational approaches in the genomic era, Trends in Biotech. 18: 34-39, 2000.*
Pan et al., J. Protein Chem., 1999, 18(5): 579-584.*
Sudarsanam, Proteins: Structure, Function, and Genetics, 1998, 30:228-231.*
Fink et al., "Human microtubule-associated protein 1a (MAP1A) gene: Genomic organization, cDNA sequence, and developmental and tissue-specific expression," *Genomics* 35:577-585 (1996).
Redenbach et al., "A set of ordered cosmids and a detailed genetic and physical map for the 8 Mb *Streptomyces coelicolor* A3(2) chromosome," *Molecular Microbiol.* 21:77-96 (1996).
Ruoslahti, "Targeting tumor vasculature with homing peptides from phage display," *Sem. Cancer Biology* 10:435-442 (2000).
Antman K., "Randomized Trials of High Dose Chemotherapy for Breast Cancer," *Biochimica et Biophysica Acta* 1471:M89-M98 (2001).
Arap et al., "Cancer Treatment by Targeted Drug Delivery to Tumor Vasculature in a Mouse Model," *Science* 279:377-380 (1998).
Burris III, "Docetaxel (Taxotere) Plus Trastuzumab (Herceptin) in Breast Cancer," *Semin. Oncol.* 28(suppl 3):38-44 (2001).
Chan et al., "Prospective Randomized Trial of Docetaxel Versus Doxorubicin in Patients with Metastatic Breast Cancer. The 303 Study Group," *J. Clin. Oncol.* 17:2341-2354 (1999).
Chen et al., "RGD-Tachyplesin Inhibits Tumor Growth," *Cancer Res.* 61:2434-2438 (2001).
Cottrell et al., "Cloning, Expression, and Characterization of Human Cytosolic Aminopeptidase P: A Single Manganese (II)-Dependent Enzyme," *Biochemistry* 39:15121-15128 (2000).
Cottrell et al., "Identification of Critical Residues in the Active Site of Porcine Membrane-Bound Aminopeptidase P," *Biochemistry* 39:15129-15135 (2000).
Crown J., "The Platinum Agents: A Role in Breast Cancer Treatment?," *Semin. Oncol.* 28(suppl 3):28-37(2001).
Curnis et al., "Enhancement of Tumor Necrosis Factor α Antitumor Immunotherapeutic Properties by Targeted Delivery to Aminopeptidase N (CD13)," *Nature Biotech.* 18:1185-1190 (2000).
Dehm and Nordwig, "The Cleavage of Prolyl Peptides by Kidney Peptidases. Partial Purification of an "X-Prolyl-Aminopeptidase" from Swine Kidney Microsomes," *Eur. J. Biochem.* 17:364-371 (1970).
Ellerby et al., "Anti-cancer activity of targeted pro-apoptotic peptides," *Nat. Med.* 5:1032-1038 (1999).
Fisher et al., "Tamoxifen for Prevention of Breast Cancer: Report of the National Surgical Adjuvant Breast and Bowel Project P-1 Study," *J. Natl. Cancer Instit.* 90:1371-1388.
GenBank Accession No. NP_002364.2—microtubule-associated protein 1A; microtubule-associated protein 1-like [*Homo sapiens*].
GenBank Accession No. P78559—microtubule-associated protein 1A [Contains: Map1 light chain LC2].
GenBank Accession No. NP_114124.1—BTE-binding protein 4 [*Homo sapiens*].
GenBank Accession No. AAB41132.1—(U38291) microtubule-associated protein 1a [*Homo sapiens*].
GenBank Accession No. AAD00355.1—microtubule associated proein 1A [*Homo sapiens*].
GenBank Accession No. CAB61610.1—putative acyl-CoA dehydrogenase [*Streptomyces coelicolor* A3(2)].

(Continued)

*Primary Examiner*—Larry R Helms
*Assistant Examiner*—Hong Sang
(74) *Attorney, Agent, or Firm*—McDermott Will & Emery LLP

(57) ABSTRACT

The present invention provides a method of directing a moiety to breast vasculature in a subject by administering to the subject a conjugate which contains a moiety linked to a homing molecule that selectively homes to breast vasculature, whereby the moiety is directed to breast vasculature. In one embodiment, the homing molecule is a peptide containing the amino acid sequence PGPEGAG (SEQ ID NO: 1), or a peptidomimetic thereof.

28 Claims, 10 Drawing Sheets

OTHER PUBLICATIONS

Harbeck and Mentlein, "Aminopeptidase P from Rat Brain. Purification and Action on Bioactive Peptides," *Eur. J. Biochem.* 198:451-458 (1991).

Hawthorne et al., "Evaluation of some Fluorogenic Substrates for continuous Assay of Aminopeptidase P," *Analytical Biochemistry* 253:13-17 (1997).

Hooper et al., "Purification and Characterization of Pig Kidney Aminopeptidase P. A Glycosyl-Phosphatidylinositol-Anchored Ectoenzyme," *Biochem. J.* 267:509-515 (1990).

Hyde et al., "Molecular Cloning and Expression in Cos-1 Cells of Pig Kidney Aminopeptidase P," *Biochem. J.* 319:197-201 (1996).

Koivunen et al., "Tumor Targeting with a Selective Gelatinase Inhibitor," *Nat. Biotechnol.* 17:768-774 (1999).

Lasch et al., "Aminopeptidase P—a Cell-Surface Antigen of Endothelial and Lymphoid Cells: Catalytic and Immuno-Histotopical Evidences," *Biol. Chem.* 379:705-709 (1998).

Lloyd et al., "Inhibition and Metal Ion Activation of Pig Kidney Aminopeptidase P. Dependence on Nature of Substrate," *Biochem. Pharmacol.* 52:229-236 (1996).

Maggiora et al., "Apstatin Analogue Inhibitors of Aminopeptidase P, a Bradykinin-Degrading Enzyme," *J. Med. Chem.* 42:2394-2402 (1999).

Orawski and Simmons, "Purification and Properties of Membrane-bound Aminopeptidase P from Rat Lung," *Biochemistry* 34:11227-11236 (1995).

Paridaens et al., "Paclitaxel Versus Doxorubicin as First-Line Single-Agent Chemotherapy for Metastatic Breast Cancer: a European Organization for Research and Treatment of Cancer Randomized Study with Cross-over," *J. Clin. Oncol.* 18:724-733 (2000).

Pasqualini and Ruoslahti, "Organ Targeting in Vivo Using Phage Display Peptide Libraries," *Nature* 380:360-364 (1996).

Pasqualini et al., "Aminopeptidase N Is a Receptor for Tumor-homing Peptides and a Target for Inhibiting Angiogenesis," *Cancer Res.* 60:722-727 (2000).

Rajotte and Ruoslahti, "Membrane Dipeptidase Is the Receptor for a Lung-Targeting Peptide Identified by in Vivo Phage Display," *J. Biol. Chem.* 274:11593-11598 (1999).

Romero et al., "Purification and Amino Acid Sequence of Aminopeptidase P from Pig Kidney," *Eur. J. Biochem.* 229:262-269 (1995).

Rajotte et al., "Molecular Heterogeneity of the Vascular Endothelium Revealed by in Vivo Phage Display," *J. Clin. Invest.* 102:430-437 (1998).

Rusu and Yaron, "Aminopeptidase P from Human Leukocytes," *Eur. J. Biochem.* 210:93-100 (1992).

Ryan et al., "Immunoaffinity Purifications of Aminopeptidase P from Guinea Pig Lungs, Kidney and Serum," *Biochem. Biophys. Res. Com.* 205:1796-1802 (1994).

Ryan et al., "Purification and Characterization of Guinea Pig Serum Aminoacylproline Hydrolase (Aminopeptidase P)," *Biochim. Biophys. Acta* 1119:140-147 (1992).

Ryan et al., "Aminopeptidase P Is Disposed on Human Endothelial Cells," *Immunopharmacol.* 32:149-152 (1996).

Samoylova and Smith, "Elucidation of muscle-binding peptides by phage display screening," *Muscle Nerve* 22:460-466 (1999).

Simmons and Orawski, "Membrane-bound Aminopeptidase P from Bovine Lung. Its Purification, Properties, and Degradation of Bradykinin," *J. Biol. Chem.* 267:4897-4903 (1992).

Stöckel et al., "Specific Inhibitors of Aminopeptidase P," *Cellular Peptidases in Immune Functions and Diseases*, (eds. Ansorge and Langner), Plenum Press, New York, pp. 31-35 (1997).

Vanhoof et al., "Proline Motifs in Peptides and their Biological Processing," *FASEB J.* 9:736-744 (1995).

Vanhoof et al., "Distribution of Proline-specific Aminopeptidases in Human Tissues and Body Fluids," *Eur. J. Clin. Chem. Clin. Biochem.* 30:333-338 (1992).

Vanhoof, "Kininase Activity in Human Platelets: Cleavage of the Argl-Pro2 Bond of Bradykinin by Aminopeptidase P," *Biochem. Pharmacol.* 44:479-487 (1992).

Venema et al., "Cloning and Tissue Distribution of Human Membrane-Bound Aminopeptidase P," *Biochimica et Biophysica Acta* 1354:45-48 (1997).

Vicini et al., "Accelerated Treatment of Breast Cancer," *Journal of Clinical Oncology* 19:1993-2001 (2001).

White et al., "Antibody-Targeted Immunotherapy for Treatment of Malignancy," *Annu. Rev. Med.* 52:125-145 (2001).

Wolff A., "Systemic Therapy," *Current Opinion in Oncology* 12:532-540 (2000).

Yoshimoto et al., "Substrate Specificity of Aminopeptidase P from *Escherichia coli*: Comparison with Membrane-bound Forms from Rat and Bovine Lung," *Arch. Biochem. Biophys.* 311:28-34 (1994).

\* cited by examiner

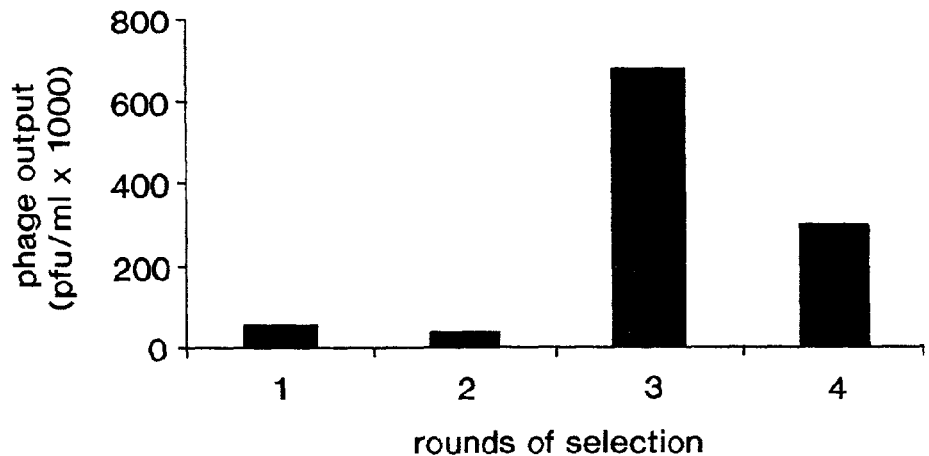
FIG. 4A
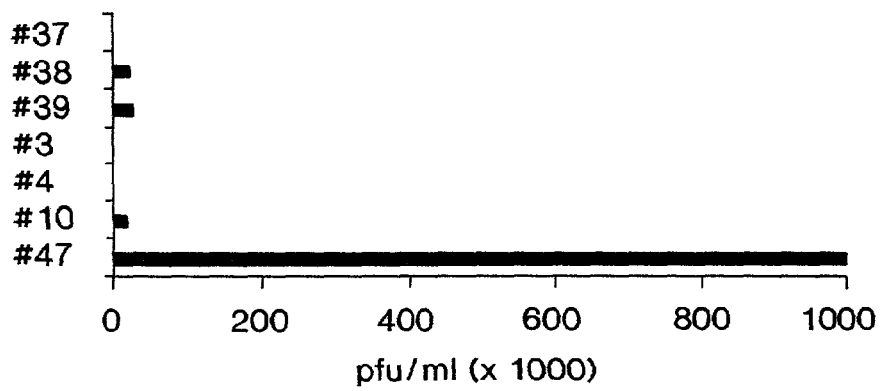
FIG. 4B
AmPaseP (AS 1-22)    M A R A H W G C P W L V L L C A C A W G H T
Clone #47            F M A R A S - G C P - L V L R C A C D C - H T
AmPaseP (AS 23-42)   K P V D L G G Q D V R N C S
Clone #47            G N V - L G G Q D - C N C S
FIG. 4C

```
cacccuatcc tacactacta ggaacttgca cagtccgcct cgggcagccc aaagctcctc  60
tgcccaccct ggctcccaaa accctccaaa acaaaagacc agaaaagcac tctccaccca  120
gcagccaaac gcctccttct tgacgccagc ccccaccctc tgtctgctcg agcccaggaa  180
aggcctgaag gaacaggccg gggaaggagc cctccctctc tcccttgtcc ctccatccac  240
ccagcgccgg catctggaga ccctatggcc cgggctcact ggggctgctg cccctggctg  300
gtcctcctct gtgcttgtgc ctggggccac acaaagccac tggaccttgg agggcaggat  360
gtgagaaatt gttccaccaa ccccccttac cttccagtta ctgtggtcaa taccacaatg  420
tcactcacag ccctccgcca gcagatgcag acccagaatc tctcagccta catcatccca  480
ggcacagatg ctcacatgaa cgagtacatc ggccaacatg acgagaggcg tgcgtggatt  540
acaggcttta cagggtctgc aggaactgca gtggtgacta tgaagaaagc agctgtctgg  600
accgacagtc gctactggac tcaggctgag cggcaaatgg actgtaattg ggagctccat  660
aaggaagttg gcaccactcc tattgtcacc tggctcctca ccgagattcc cgctggaggg  720
cgtgtgggtt ttgaccccctt cctcttgtcc attgacacct gggagagtta tgatctggcc  780
ctccaaggct ctaacagaca gctggtgtcc atcacaacca atcttgtgga cctggtatgg  840
ggatcagaga ggccaccggt tccaaatcaa cccatttatg ccctgcagga ggcattcaca  900
gggagcactt ggcaggagaa agtatctggc gtccgaagcc agatgcagaa gcatcaaaag  960
gtcccgactg ccgtccttct gtcggcgctt gaggagacgg cctggctctt caaccttcga 1020
gccagtgaca tccctataa ccccttcttc tattcctaca cgctgctcac agactcttct 1080
attaggttgt ttgcaaacaa gagtcgcttt agctccgaaa ccttgagcta tctgaactcc 1140
agttgcacag gccccatgtg tgtgcaaatc gaggattaca gccaagttcg tgacagcatc 1200
caggcctact cattgggaga tgtgaggatc tggattggga ccagctatac catgtatggg 1260
atctatgaaa tgataccaag ggagaaactc gtgacagaca cctactcccc agtgatgatg 1320
accaaggcag tgaagaacag caaggagcag gccctcctca aggccagcca cgtgcgggac 1380
gctgtggctg tgatccggta cttggtctgg ctggagaaga acgtgcccaa aggcacagtg 1440
gatgagtttt cgggggcaga gatcgtggac aagttccgag agaagaaca gttctcctcc 1500
ggacccagtt ttgaaaccat ctctgctagt ggtttgaatg ctgccctggc ccactacagc 1560
ccgaccaagg agctgaaccg caagctgtcc tcagatgaga tgtacctgct ggactctggg 1620
gggcagtact gggacgggac cacagacatc accagaacag tccactgggg caccccctct 1680
gcctttcaga aggaggcata tacccgtgtg ctgataggaa atattgacct gtccaggctc 1740
atctttcccg ctgctacatc agggcgaatg gtggaggcct tgcccgcag agccttgtgg 1800
gatgctggtc tcaattatgg tcatgggaca ggccacggca ttggcaactt cctgtgtgtg 1860
catgagtggc cagtgggatt ccagtccaac aacatcgcta tggccaaggg catgttcact 1920
tccattgaac ctggttacta taaggatgga gaatttggga tccgtctcga agatgtggct 1980
```

FIG. 7A-1

```
ctcgtggtag aagcaaagac caagtaccca gggagctacc tgacctttga agtggtatca 2040
tttgtgccct atgaccggaa cctcatcgat gtcagcctgc tgtctcccga gcatctccag 2100
tacctgaatc gctactacca gaccatccgg gagaaggtgg gtccagagct gcagaggcgc 2160
cagctactag aggagttcga gtggcttcaa cagcacacag agccctggc cgccagggcc 2220
ccagacaccg cctcctgggc ctctgtgtta gtggtctcca cccttgccat ccttggctgg 2280
agtgtctaga ggctccagac tctcctgtta accctccatc tagatggggg gctcccttgc 2340
ttagctcccc tcaccctgca ctgaacatac ccaagagcc cctgctggcc cattgcctag 2400
aaaccttttgc attcatcctc cttctccaag acctatggag aaggtcccag gccccaggaa 2460
acacagggct tcttggcccc agatggcacc tccctgcacc ccggggttgt ataccacacc 2520
ctgggcccct aatcccaggc ccgaaatag gaaagccagc tagtctcttc tcttctgtga 2580
tctcagtagg cctaacctat aacctaacac agactgctac agctgctccc ctcccgccaa 2640
acaaagcccc aagaaaacaa tgccctacc acccaagggt gccatggtcc cgggaaaacc 2700
caacctgtca ccgcgtgttg ggcgtaacca gaactgttcc cccccaccag ggcttaaaaa 2760
tcgcccccac tttttaacca tcgtccatta accacctggt gggcatagcc agagctgttc 2820
gaacccagcc agggatgaaa aatcaacccc cgacatggaa cccatgattc ctaaacccgg 2880
ggtaggttcc atgccaagta acagcagagg gagttaagcc ataggaattt ggctgtggag 2940
taagagggaa tgcggtgagg cagtgtggaa tatgacccta ccagaggttg agaacaaac 3000
ttgggcagcc ggaacccgtc actattttag attcctggca ttcgaggagc cctttgaact 3060
ttccaaagtg cagccacagc tacaatgctg ttaaatcctc ccacatttct tggatgcccc 3120
ttcaccttgt gtggacagtg tctggtttcc ccattttaca gacaggaaaa ctgagcttca 3180
gacaggtggt gggctttgcc taaggacaca caaatttggt tgggagttga tggggccaga 3240
tgagccagca ttccagctgt ttcacccttc agcaacatgc agagtccctg agcccacctc 3300
ccagccctct cctcattctc tgaacccact gtggtgagaa gaatttgctc cggccaaatt 3360
ggccgttagc cacctgggtc cacatcctgc taagacgttt aaaacagcct aacaaagaca 3420
cttgcctgtg g
```

FIG. 7A-2

MARAHWGCCPWLVLLCACAWGHTKPLDLGGQDVRNCSTNPPYLPVTVVNTTMSLTALRQQMQTQNLSAYI
IPGTDAHMNEYIGQHDERRAWITGFTGSAGTAVVTMKKAAVWTDSRYWTQAERQMDCNWELHKEVGTTPI
VTWLLTEIPAGGRVGFDPFLLSIDTWESYDLALQGSNRQLVSITTNLVDLVWGSERPPVPNQPIYALQEA
FTGSTWQEKVSGVRSQMQKHQKVPTAVLLSALEETAWLFNLRASDIPYNPFFYSYTLLTDSSIRLFANKS
RFSSETLSYLNSSCTGPMCVQIEDYSQVRDSIQAYSLGDVRIWIGTSYTMYGIYEMIPREKLVTDTYSPV
MMTKAVKNSKEQALLKASHVRDAVAVIRYLVWLEKNVPKGTVDEFSGAEIVDKFRGEEQFSSGPSFETIS
ASGLNAALAHYSPTKELNRKLSSDEMYLLDSGGQYWDGTTDITRTVHWGTPSAFQKEAYTRVLIGNIDLS
RLIFPAATSGRMVEAFARRALWDAGLNYGHGTGHGIGNFLCVHEWPVGFQSNNIAMAKGMFTSIEPGYYK
DGEFGIRLEDVALVVEAKTKYPGSYLTFEVVSFVPYDRNLIDVSLLSPEHLQYLNRYYQTIREKVGPELQ
RRQLLEEFEWLQQHTEPLAARAPDTASWASVLVVSTLAILGWSV

FIG. 7B

BREAST HOMING PEPTIDES AND METHODS OF IDENTIFYING SAME USING AMINOPEPTIDASE P

This application is based on, and claims the benefit of, U.S. Provisional Application No. 60/453,687, filed Jun. 1, 2001, which was converted from U.S. Ser. No. 09/872,342, and which is incorporated herein by reference.

This invention was made with government support under CA74238, CA82715 and Cancer Center Support Grant CA 30199 from the National Cancer Institute. The government has certain rights in this invention.

BACKGROUND OF THE INVENTION

1. Field of the Invention

The present invention relates generally to the fields of molecular medicine and drug delivery and, more specifically, to molecules that selectively home to the vasculature of mammary tissue.

2. Background Information

A major hurdle to advances in treating breast cancer is the relative lack of agents that can selectively target the cancer while sparing normal tissue. For example, radiation therapy and surgery-, which generally are localized treatments, can cause substantial damage to normal tissue in the treatment field, resulting in scarring and loss of normal tissue. Chemotherapy, in comparison, which generally is administered systemically, can cause substantial damage to organs such as bone marrow, mucosae, skin and the small intestine, which undergo rapid cell turnover and continuous cell division. As a result, undesirable side effects such as nausea, loss of hair and drop in blood cell count can occur as a result of the systemic treatment of a breast cancer patient with a chemotherapeutic agent. Such undesirable side effects often limit the amount of a treatment that can be safely administered, thereby hampering survival rate and impacting the quality of patient life.

As an example, estrogen receptor positive cancer often is treated with the estrogen receptor modulator agent, tamoxifen. However, potential risks associated with tamoxifen treatment include endometrial cancer and thromboembolic disease. Similarly, the use of the platinum agent, cisplatin, can be limited by the severe nausea, vomiting, neuropathy and myelosuppression that accompany administration of this drug. Other agents for treatment of breast cancer similarly are accompanied by undesirable side effects due to the fact that they cannot be specifically delivered to the breast without also reaching other organs of the patient.

It is clear that there is a strong genetic component to the etiology of most types of malignant tumors, including breast cancer. Mutations in the tumor suppressor genes BRCA-1, BRCA-2 and p53, for example, contribute to predisposition to breast cancer. Familial occurrence, tests for mutated tumor suppressor genes and the diagnosis of lobular carcinoma in situ define a population of women at high risk of developing breast cancer. Currently, the only effective strategy for preventive treatment of these women at high risk is preventive mastectomy. Thus, there is a need for simpler and less invasive procedures for selectively ablating breast tissue, for example, as a preventive measure in women at high risk or to treat pre-malignant or early breast cancer.

The present invention satisfies this need by providing molecules that selectively home to breast vasculature and which are suitable for selectively targeting agents for cell ablation or other chemotherapeutic agents to breast tissue, particularly to breast vasculature. Related advantages also are provided.

SUMMARY OF THE INVENTION

The present invention provides a method of directing a moiety to breast vasculature in a subject by administering to the subject a conjugate which contains a moiety linked to a homing molecule that selectively homes to breast vasculature, whereby the moiety is directed to breast vasculature. In a method of the invention, the homing molecule can be, for example, a peptide or peptidomimetic. In one embodiment, the homing molecule is a peptide containing the amino acid sequence PGPEGAG (SEQ ID NO: 1), or a peptidomimetic thereof. In other embodiments, the homing molecule is a peptide that contains the amino acid sequence CRSS (SEQ ID NO: 3) or the amino acid sequence CRTS (SEQ ID NO: 4), or a peptidomimetic of one of these sequences.

In specific embodiments, a method of the invention for directing a moiety to breast vasculature is practiced with a homing peptide having a length of at most 10 or 20 amino acids. In additional embodiments, a method of the invention is practiced with a homing peptide containing the amino acid sequence PGPEGAG (SEQ ID NO: 1) and having a length of at most 10 or 20 amino acids. In additional embodiments, a method of the invention is practiced with a homing peptide containing the amino acid sequence CRSS (SEQ ID NO: 3) and having a length of at most 10 or 20 amino acids. In still further embodiments, a method of the invention is practiced with a homing peptide containing the amino acid sequence CRTS (SEQ ID NO: 4) and having a length of at most 10 or 20 amino acids. In yet further embodiments, the invention is practiced with a cyclic homing peptide or peptidomimetic, for example, a cyclic peptide containing the amino acid sequence PGPEGAG (SEQ ID NO: 1) or a peptidomimetic thereof; a cyclic peptide containing the amino acid sequence CRSS (SEQ ID NO: 3) or a peptidomimetic thereof; or a cyclic peptide containing the amino acid sequence CRTS (SEQ ID NO: 4) or a peptidomimetic thereof.

A variety of moieties can be directed to breast vasculature by a method of the invention. Such a moiety can be, for example, a therapeutic agent, cancer chemotherapeutic agent, pro-apoptotic agent, cytotoxic agent or detectable label. In specific embodiments, a method of the invention is practiced with a conjugate containing a homing peptide or peptidomimetic linked to a moiety which is a therapeutic agent, cancer chemotherapeutic agent, pro-apoptotic agent, cytotoxic agent or detectable label. In other embodiments, a method of the invention is practiced with a conjugate that includes a homing peptide containing the amino acid sequence PGPEGAG (SEQ ID NO: 1), or a peptidomimetic thereof, linked to a moiety which is a therapeutic agent, cancer chemotherapeutic agent, pro-apoptotic agent, cytotoxic agent or detectable label. In further embodiments, a method of the invention is practiced with a conjugate that includes a homing peptide containing the amino acid sequence CRSS (SEQ ID NO: 3) or CRTS (SEQ ID NO: 4), or a peptidomimetic of one of these sequences, linked to a moiety which is a therapeutic agent, cancer chemotherapeutic agent, pro-apoptotic agent, cytotoxic agent or detectable label.

The invention further provides a method of directing a moiety to breast vasculature in a subject by administering to the subject a conjugate containing a moiety linked to a homing molecule that specifically binds aminopeptidase P, whereby the moiety is directed to breast vasculature. Such a method can be practiced, for example, with a homing molecule that is a peptide or peptidomimetic. In one embodiment, a homing molecule that specifically binds aminopeptidase P is a peptide containing the amino acid sequence PGPEGAG (SEQ ID NO: 1), or a peptidomimetic thereof. The invention can be practiced with a homing peptide having a length, for example, of at most 10 or 20 amino acids. For example, the invention can be practiced with a homing peptide containing the amino acid sequence PGPEGAG (SEQ ID NO: 1) and having a length of at most 10 or 20 amino acids. In specific embodiments, the homing molecule that specifically binds aminopeptidase P is a cyclic peptide or peptidomimetic, for example, a cyclic peptide containing the amino acid sequence PGPEGAG (SEQ ID NO: 1), or a peptidomimetic thereof. In another embodiment, the homing molecule that specifically binds aminopeptidase P is a selective inhibitor of aminopeptidase P.

In a method of the invention for directing a moiety to breast vasculature in a subject, the conjugate can contain a moiety which is, for example, a therapeutic agent, cancer chemotherapeutic agent, pro-apoptotic agent, cytotoxic agent or detectable label. In specific embodiments, the invention is practiced with a conjugate that contains a homing peptide or peptidomimetic linked to a moiety which is a therapeutic agent, cancer chemotherapeutic agent, pro-apoptotic agent, cytotoxic agent or detectable label. In further embodiments, the invention is practiced with a conjugate that contains a homing peptide including the amino acid sequence PGPEGAG (SEQ ID NO: 1), or a peptidomimetic thereof, linked to a moiety which is a therapeutic agent, cancer chemotherapeutic agent, pro-apoptotic agent, cytotoxic agent or detectable label.

Further provided by the invention is a method of imaging breast vasculature in a subject. The method includes the steps of administering to the subject a conjugate containing a detectable label linked to a molecule that specifically binds aminopeptidase P, whereby the conjugate specifically binds breast vasculature; and detecting the conjugate. In a method of the invention for imaging breast vasculature, the homing molecule can be, for example, a peptide or peptidomimetic, such as a peptide comprising the amino acid sequence PGPEGAG (SEQ ID NO: 1), or a peptidomimetic thereof, and, if desired, can be a cyclic peptide or peptidomimetic. A homing peptide useful in the invention, such as a peptide including the amino acid sequence PGPEGAG (SEQ ID NO: 1), can have a length of, for example, at most 10 or 20 amino acids. In one embodiment, the homing molecule that specifically binds aminopeptidase P is a selective inhibitor of of aminopeptidase P. A variety of detectable labels are useful in the imaging methods of the invention, including, for example, indium-111, technitium-99, carbon-11 and carbon-13.

The invention further provides an isolated homing peptide that selectively homes to breast vasculature, which contains an amino acid sequence that has a length of less than 50 amino acids. An isolated homing peptide of the invention can have a variety of lengths, for example, at most 10 or at most 20 amino acids and, if desired, can be cyclic.

The invention additionally provides an isolated homing molecule having a length of less than 50 amino acids that selectively homes to breast vasculature and contains the amino acid sequence PGPEGAG (SEQ ID NO: 1), or a peptidomimetic thereof. In one embodiment, the invention provides an isolated homing peptide having a length of less than 50 amino acids that selectively homes to breast vasculature and contains the amino acid sequence PGPEGAG (SEQ ID NO: 1). In another embodiment, the invention provides an isolated homing molecule having a length of less than 50 amino acids that selectively homes to breast vasculature and contains the amino acid sequence CPGPEGAGC (SEQ ID NO: 2), or a peptidomimetic thereof. Any of the above homing peptides can be useful as short peptides, for example, having a length of at most 10 or 20 amino acids, and, if desired, can be cyclic.

The invention also provides an isolated homing molecule having a length of less than 50 amino acids that selectively homes to breast vasculature and contains the amino acid sequence CRSS (SEQ ID NO: 3) or CRTS (SEQ ID NO: 4), or a peptidomimetic of one of these sequences. In one embodiment, the invention provides an isolated homing peptide having a length of less than 50 amino acids that selectively homes to breast vasculature and contains the amino acid sequence CRSS (SEQ ID NO: 3). In another embodiment, the invention provides an isolated homing peptide having a length of less than 50 amino acids that selectively homes to breast vasculature and contains the amino acid sequence CRTS (SEQ ID NO: 4).

Further provided by the invention is a conjugate which contains a moiety linked to a homing molecule that selectively homes to breast vasculature. A homing molecule useful in the conjugate of the invention can be, for example, a peptide or peptidomimetic. In specific embodiments, a conjugate of the invention includes a homing peptide containing the amino acid sequence the amino acid sequence PGPEGAG (SEQ ID NO: 1), CPGPEGAGC (SEQ ID NO: 2), CRSS (SEQ ID NO: 3) or CRTS (SEQ ID NO: 4), or a peptidomimetic of one of these sequences. In one embodiment, a conjugate of the invention includes a homing peptide containing the amino acid sequence CRSS (SEQ ID NO: 3). In another embodiment, a conjugate of the invention includes a homing peptide containing the amino acid sequence CRTS (SEQ ID NO: 4). In a further embodiment, a conjugate of the invention contains a homing molecule that selectively binds aminopeptidase P. In yet a further embodiment, a conjugate contains a homing molecule which is a selective inhibitor of aminopeptidase P such as apstatin or an analog thereof.

Where a conjugate contains a homing peptide, the peptide can have, for example, a length of at most 10 or 20 amino acids. If desired, a homing molecule used in a conjugate of the invention can be cyclic. A variety of moieties are useful in a conjugate of the invention including, for example, therapeutic agents, cancer chemotherapeutic agents, pro-apoptotic agents, cytotoxic agents, and detectable labels.

The invention also provides a method of identifying a homing molecule that selectively homes to breast vasculature by contacting aminopeptidase P with one or more molecules; and determining specific binding of a molecule to aminopeptidase P, where the presence of specific binding identifies at least one of the molecules as a homing molecule that selectively homes to breast vasculature. A method of the invention for identifying a homing molecule that selectively homes to breast vasculature can be practiced, for example, with substantially purified aminopeptidase P. In one embodiment, the invention is practiced with aminopeptidase P immobilized on a support. In another embodiment, the invention is practiced with human aminopeptidase P.

The invention further provides a method of identifying a homing molecule that selectively homes to breast vasculature by contacting aminopeptidase P and a peptide containing the amino acid sequence PGPEGAG (SEQ ID NO: 1), or a peptidomimetic thereof, with one or more molecules; and determining specific binding of the peptide or peptidomimetic to aminopeptidase P in the presence of the one or more molecules as compared to binding in the absence of the one or more molecules, where inhibition of specific binding identifies at least one of the molecules as a homing molecule that selectively homes to breast vasculature. In a method of the invention, the aminopeptidase P can be, for example, substantially purified. In one embodiment, the aminopeptidase P is human aminopeptidase P.

Further provided by the invention is a method of identifying a homing molecule that selectively homes to breast vasculature by contacting aminopeptidase P with one or more molecules; and determining selective inhibition of aminopeptidase P by at least one of the molecules, where the presence of selective inhibition identifies at least one of the molecules as a homing molecule that selectively homes to breast vasculature. The aminopeptidase P can be, for example, substantially purified aminopeptidase P. In one embodiment, the aminopeptidase P is immobilized on a support. In another embodiment, the aminopeptidase P is human aminopeptidase P.

BRIEF DESCRIPTION OF THE DRAWINGS

FIG. 4 shows isolation of cDNA clones encoding CPGPEGAGC (SEQ ID NO: 2)-binding proteins. (A) The CPGPEGAGC (SEQ ID NO: 2) peptide was covalently linked to microtiter wells, and a phage cDNA library screened for clones that bound to the peptide by performing four consecutive rounds of selection. The number of pfu recovered from the wells is shown. (B) Clones from the screening shown in panel A were tested individually for binding to wells coated with the CPGPEGAGC (SEQ ID NO: 2) peptide. (C) Comparison of residues 1 to 42 of aminopeptidase P (SEQ ID NO: 5) to clone #47 (SEQ ID NO: 6).

FIG. 7 shows the nucleotide (SEQ ID NO: 7) and amino acid (SEQ ID NO: 8) sequence of human membrane-bound aminopeptidase P.

DETAILED DESCRIPTION OF THE INVENTION

The present invention is directed, in part, to the discovery of homing molecules that selectively home to the vasculature of breast tissue. As disclosed herein, peptides CPGPEGAGC (SEQ ID NO: 2), CRSS (SEQ ID NO: 3) and CRTS (SEQ ID NO: 4) were identified by in vivo panning as selectively homing to breast tissue as compared to control pancreatic tissue. About 100 times more of the CPGPEGAGC (SEQ ID NO: 2)-displaying phage than control T7 phage homed to breast and, furthermore, the CPGPEGAGC (SEQ ID NO: 2) phage did not home to most other tissues, including pancreas, brain, kidney, lung and skin from parts of the body other than the breast fat pad (see FIG. 2). As further disclosed herein, breast homing of the CPGPEGAGC (SEQ ID NO: 2) phage was specific, since coinjection of free peptide SEQ ID NO: 2 markedly reduced recovery of CPGPEGAGC (SEQ ID NO: 2)-bearing phage from breast tissue (see Example I and FIG. 2).

Figure 3A:
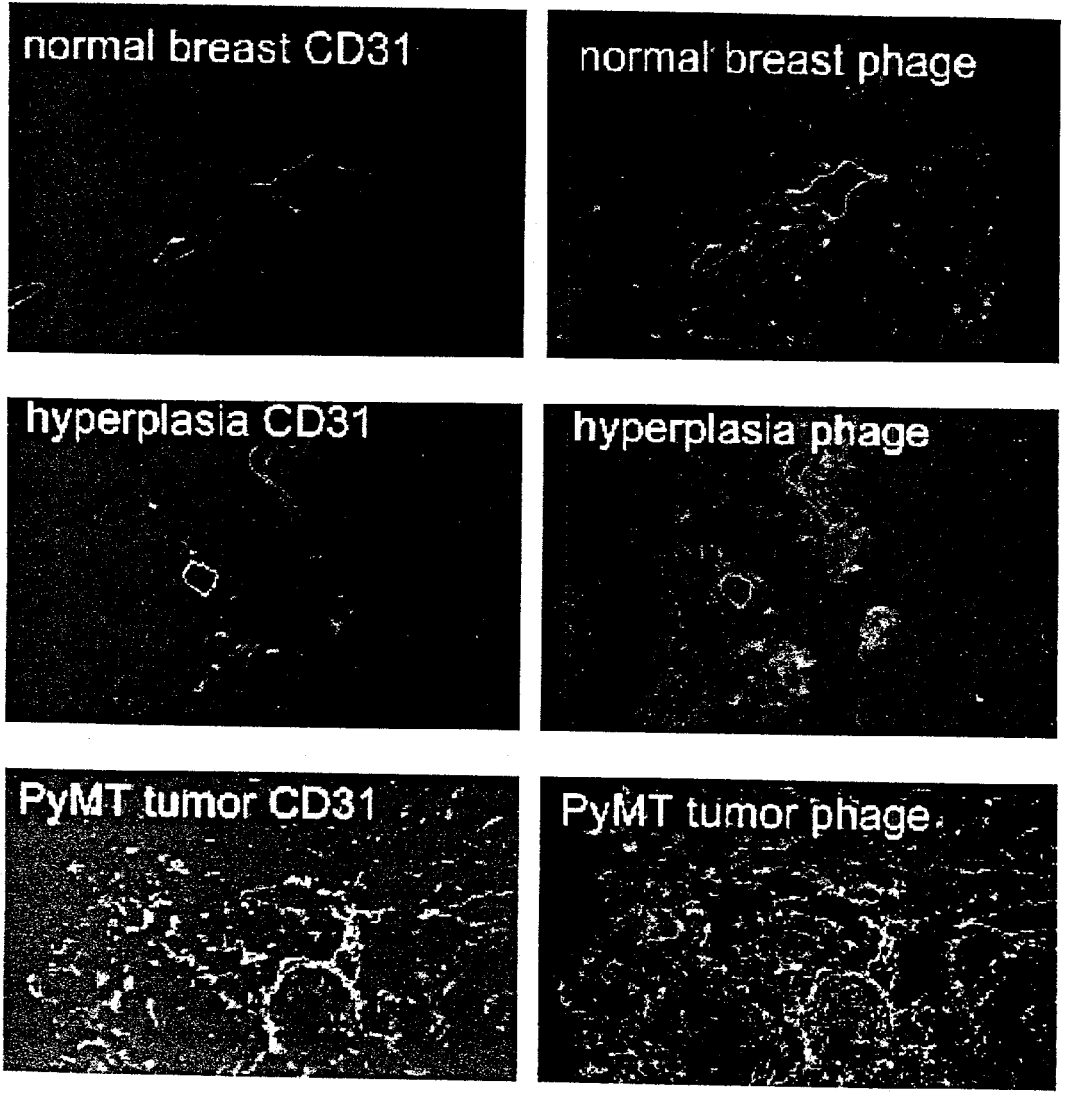
FIG. 3 shows localization of CPGPEGAGC (SEQ ID NO: 2) binding using phage overlay assays. Cryo-sections from normal mouse breast tissue, hyperplastic breast tissue, MMTV PyMT breast carcinomas (A) or metastases from MMTV PyMT carcinomas (B) were incubated with CPGPEGAGC (SEQ ID NO: 2) phage suspension ($10^{10}$ pfu/ml). Phage binding to the tissue sections was visualized with rabbit anti-T7 antiserum and FITC-labeled goat anti-rabbit antibody. The sections were co-stained for CD31 with mouse monoclonal anti-CD31 and TRITC-conjugated anti-mouse IgG antibody.
Figure 3B:
Figure 3B:
Figure 3B:
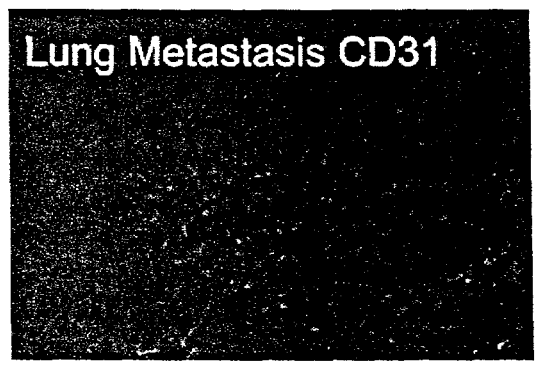
Figure 3B:
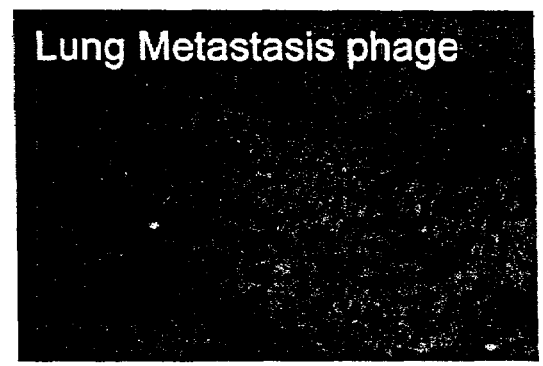

As further disclosed herein in Example II, peptide CPGPEGAGC (SEQ ID NO: 2) selectively homed to the vascular endothelium of mammary tissue. As shown in FIG. 3A, phage overlay of tissue sections stained with the endothelial marker, CD-31, revealed co-localization of breast homing phage bearing CPGPEGAGC (SEQ ID NO: 2) with the endothelial marker. The SEQ ID NO: 2 bearing phage also co-localized with CD-31 in hyperplastic mammary tissue of breast cancers that developed in MMTV PyMT mice, although not to the vasculature of lung or liver metastases in these mice (see FIG. 3B). These results demonstrate that CPGPEGAGC (SEQ ID NO: 2)-bearing phage home to the vascular endothelium of breast tissue.

Figure 5A:
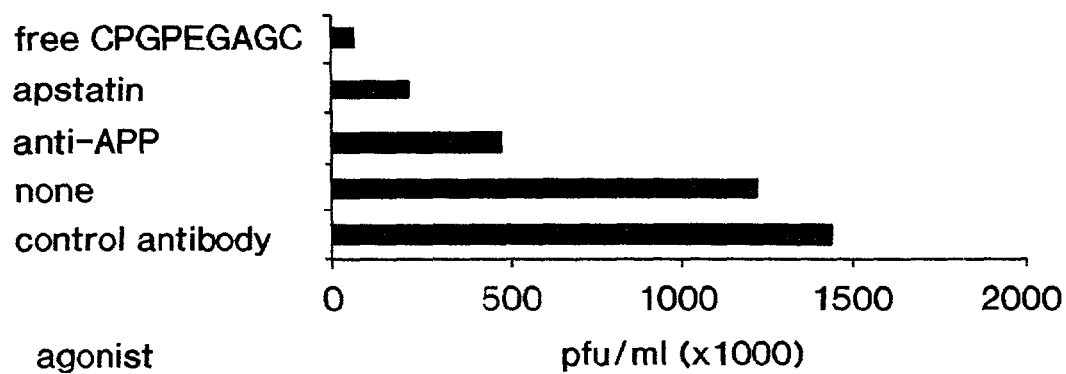
FIG. 5 shows that free CPGPEGAGC (SEQ ID NO: 2) peptide, anti-aminopeptidase P antibody and a chemical aminopeptidase P inhibitor block binding of CPGPEGAGC (SEQ ID NO: 2) phage to aminopeptidase P in vitro and homing to breast vasculature in vivo. (A) The binding of phage displaying an aminopeptidase P cDNA fragment ($10^8$ pfu) to microtiter wells coated with CPGPEGAGC (SEQ ID NO: 2) peptide was tested in presence of 1 mg free CPGPEGAGC (SEQ ID NO: 2) peptide; the aminopeptidase P chemical inhibitor, apstatin (10 µg/ml); purified IgG from an anti-aminopeptidase P antiserum (10 µg/ml); IgG from normal rabbit serum (10 µg/ml), or buffer. (B) CPGPEGAGC (SEQ ID NO: 2)-displaying phage were injected into the tail vein of mice together with 10 µg of the anti-aminopeptidase P IgG or control IgG. (C) Recovery of another breast homing phage displaying the peptide CRSS (SEQ ID NO:3) was not modulated by anti-aminopeptidase P antiserum or by 1 mg free CPGPEGAGC (SEQ ID NO: 2) peptide.
Figure 5B:
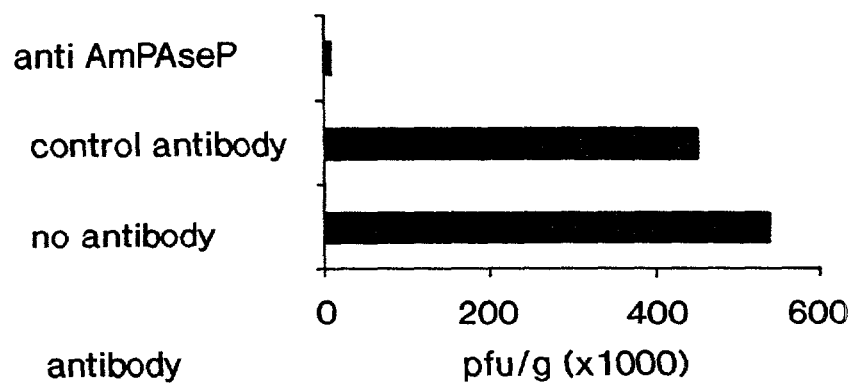

The present invention further is directed to the surprising discovery that the receptor for the CPGPEGAGC (SEQ ID NO: 2) peptide in breast vasculature is aminopeptidase P. As disclosed herein in Example III, a breast cancer cDNA library was screened against insolubilized CPGPEGAGC (SEQ ID NO: 2) peptide; phage recovery increased about 50-fold in 5 rounds of selection on the peptide, as shown in FIG. 4A. Furthermore, binding of the aminopeptidase P encoding phage to insolubilized CPGPEGAGC (SEQ ID NO: 2) peptide was blocked by incubation of phage with free peptide SEQ ID NO: 2, and independently blocked by apstatin, a synthetic inhibitor of aminopeptidase P (FIG. 5A). Binding of aminopeptidase P encoding phage also was blocked by an anti-aminopeptidase P antibody, although not by control antibody. As further shown herein in FIG. 5B, co-injection of an anti-aminopeptidase P antibody with the CPGPEGAGC (SEQ ID NO: 2) phage into mice reduced by almost 90% the number of phage subsequently rescued from the breast tissue, while a control antibody did not affect breast homing of the SEQ ID NO: 2-bearing phage. These results demonstrate that aminopeptidase P is the receptor for the CPGPEGAGC (SEQ ID NO: 2) homing molecule in breast vasculature and that aminopeptidase P can act as a receptor for homing molecules that selectively home to breast vasculature.

Based on these findings, the present invention provides homing molecules and conjugates useful for preventing, treating or reducing the severity of breast cancer. Such conjugates can be administered, for example, to a woman at high risk of developing breast cancer to reduce the amount of breast tissue. Such conjugates also can be administered, for example, to a subject having pre-malignant breast tissue or to a subject having early breast cancer.

Thus, the present invention provides a method of directing a moiety to breast vasculature in a subject by administering to the subject a conjugate which contains a moiety linked to a homing molecule that selectively homes to breast vasculature, whereby the moiety is directed to breast vasculature. In a method of the invention, the homing molecule can be, for example, a peptide or peptidomimetic. In one embodiment, the homing molecule is a peptide containing the amino acid sequence PGPEGAG (SEQ ID NO: 1), or a peptidomimetic thereof. In other embodiments, the homing molecule is a peptide containing the amino acid sequence CRSS (SEQ ID NO: 3) or CRTS (SEQ ID NO: 4), or a peptidomimetic of one of these sequences.

In specific embodiments, a method of the invention for directing a moiety to breast vasculature is practiced with a homing peptide having a length of at most 10 or 20 amino acids. In additional embodiments, a method of the invention is practiced with a homing peptide containing the amino acid sequence PGPEGAG (SEQ ID NO: 1) and having a length of at most 10 or 20 amino acids. In additional embodiments, a method of the invention is practiced with a homing peptide containing the amino acid sequence CRSS (SEQ ID NO: 3) and having a length of at most 10 or 20 amino acids. In further embodiments, a method of the invention is practiced with a homing peptide containing the amino acid sequence CRTS (SEQ ID NO: 4) and having a length of at most 10 or 20 amino acids. In yet further embodiments, the invention is practiced with a cyclic homing peptide or peptidomimetic, for example, a cyclic peptide containing the amino acid sequence PGPEGAG (SEQ ID NO: 1) or a peptidomimetic thereof; a cyclic peptide containing the amino acid sequence CRSS (SEQ ID NO: 3) or a peptidomimetic thereof; or a cyclic peptide containing the amino acid sequence CRTS (SEQ ID NO: 4) or a peptidomimetic thereof.

A variety of moieties can be directed to breast vasculature by a method of the invention. Such a moiety can be, for example, a therapeutic agent, cancer chemotherapeutic agent, pro-apoptotic agent, cytotoxic agent or detectable label. In specific embodiments, a method of the invention is practiced with a conjugate containing a homing peptide or peptidomimetic linked to a moiety which is a therapeutic agent, cancer chemotherapeutic agent, pro-apoptotic agent, cytotoxic agent or detectable label. In other embodiments, a method of the invention is practiced with a conjugate that includes a homing peptide containing the amino acid sequence PGPEGAG (SEQ ID NO: 1), or a peptidomimetic thereof, linked to a moiety which is a therapeutic agent, cancer chemotherapeutic agent, pro-apoptotic agent, cytotoxic agent or detectable label. In further embodiments, a method of the invention is practiced with a conjugate that includes a homing peptide containing the amino acid sequence CRSS (SEQ ID NO: 3) or CRTS (SEQ ID NO: 4), or a peptidomimetic of one of these sequences, linked to a moiety which is a therapeutic agent, cancer chemotherapeutic agent, pro-apoptotic agent, cytotoxic agent or detectable label.

The invention further provides a method of directing a moiety to breast vasculature in a subject by administering to the subject a conjugate containing a moiety linked to a homing molecule that specifically binds aminopeptidase P, whereby the moiety is directed to breast vasculature. In one embodiment, the invention provides a method of directing a moiety to breast vasculature in a subject by administering to the subject a conjugate containing a moiety linked to a homing molecule that specifically binds aminopeptidase P, whereby the moiety is directed to breast vasculature and provided that the homing molecule is not an antibody or antigen-binding fragment thereof.

A method of the invention can be practiced, for example, with a homing molecule that is a peptide or peptidomimetic. In one embodiment, a homing molecule that specifically binds aminopeptidase P is a peptide containing the amino acid sequence PGPEGAG (SEQ ID NO: 1), or a peptidomimetic thereof. The invention can be practiced with a homing peptide having a length, for example, of at most 10 or 20 amino acids. For example, the invention can be practiced with a homing peptide containing the amino acid sequence PGPEGAG (SEQ ID NO: 1) and having a length of at most 10 or 20 amino acids. In specific embodiments, the homing molecule that specifically binds aminopeptidase P is a cyclic peptide or peptidomimetic, for example, a cyclic peptide containing the amino acid sequence PGPEGAG (SEQ ID NO: 1), or a peptidomimetic thereof. In another embodiment, the homing molecule that specifically binds aminopeptidase P inhibits the binding of peptide PGPEGAG (SEQ ID NO: 1) to breast vasculature. In a further embodiment, the homing molecule that specifically binds aminopeptidase P is a selective inhibitor of aminopeptidase P such as apstatin or an analog thereof.

In a method of the invention for directing a moiety to breast vasculature in a subject, the conjugate can contain a moiety which is, for example, a therapeutic agent, cancer chemotherapeutic agent, pro-apoptotic agent, cytotoxic agent or detectable label. In specific embodiments, the invention is practiced with a conjugate that contains a homing peptide or peptidomimetic linked to a moiety which is a therapeutic agent, cancer chemotherapeutic agent, pro-apoptotic agent, cytotoxic agent or detectable label. In further embodiments, the invention is practiced with a conjugate that contains a homing peptide including the amino acid sequence PGPEGAG (SEQ ID NO: 1), or a peptidomimetic thereof, linked to a moiety which is a therapeutic agent, cancer chemotherapeutic agent, pro-apoptotic agent, cytotoxic agent or detectable label.

The invention further provides an isolated homing peptide that selectively homes to breast vasculature, which contains an amino acid sequence that has a length of less than 50 amino acids. An isolated homing peptide of the invention can have a variety of lengths, for example, at most 10 or at most 20 amino acids and, if desired, can be cyclic.

The invention additionally provides an isolated homing molecule having a length of less than 50 amino acids that selectively homes to breast vasculature and contains the amino acid sequence PGPEGAG (SEQ ID NO: 1), or a peptidomimetic thereof. In one embodiment, the invention provides an isolated homing peptide having a length of less than 50 amino acids that selectively homes to breast vasculature and contains the amino acid sequence PGPEGAG (SEQ ID NO: 1). In another embodiment, the invention provides an isolated homing molecule having a length of less than 50 amino acids that selectively homes to breast vasculature and contains the amino acid sequence CPGPEGAGC (SEQ ID NO: 2), or a peptidomimetic thereof. Any of the above homing peptides can be useful as short peptides, for example, having a length of at most 10 or 20 amino acids, and, if desired, can be cyclic.

The invention also provides an isolated homing molecule having a length of less than 50 amino acids that selectively homes to breast vasculature and contains the amino acid sequence CRSS (SEQ ID NO: 3), CRTS (SEQ ID NO: 4), CRSSN (SEQ ID NO: 9), CRTSN (SEQ ID NO: 10), CRSSNXXC (SEQ ID NO: 11), CRTSNXXC (SEQ ID NO: 12), CRSSNGDC (SEQ ID NO: 13), CRTSNYGC (SEQ ID NO: 14) or CR(T/S)SN(G/Y)(D/G)C (SEQ ID NO: 15), or a peptidomimetic of one of these sequences, where X is any amino acid. In one embodiment, the invention provides an isolated homing peptide having a length of less than 50 amino acids that selectively homes to breast vasculature and contains the amino acid sequence CRSS (SEQ ID NO: 3). In another embodiment, the invention provides an isolated homing peptide having a length of less than 50 amino acids that selectively homes to breast vasculature and contains the amino acid sequence CRTS (SEQ ID NO: 4). In further embodiments, the invention provides an isolated homing peptide having a length of less than 50 amino acids that selectively homes to breast vasculature and contains one of the following amino acid sequences: CRSSN (SEQ ID NO: 9), CRTSN (SEQ ID NO: 10), CRSSNXXC (SEQ ID NO: 11), CRTSNXXC (SEQ ID NO: 12), CRSSNGDC (SEQ ID NO: 13), CRTSNYGC (SEQ ID NO: 14) or CR(T/S)SN(G/Y)(D/G)C (SEQ ID NO: 15), where X is any amino acid.

Further provided by the invention is a conjugate which contains a moiety linked to a homing molecule that selectively homes to breast vasculature. A homing molecule useful in the conjugate of the invention can be, for example, a peptide or peptidomimetic. In specific embodiments, a conjugate of the invention includes a homing peptide which contains the amino acid sequence PGPEGAG (SEQ ID NO: 1), CRSS (SEQ ID NO: 3) or CRTS (SEQ ID NO: 4), or a peptidomimetic of one of these sequences. In one embodiment, a conjugate of the invention includes a homing peptide that contains the amino acid sequence CRSS (SEQ ID NO: 3). In another embodiment, a conjugate of the invention includes a homing peptide that contains the amino acid sequence CRTS (SEQ ID NO: 4). In a further embodiment, a conjugate of the invention contains a homing molecule that selectively binds aminopeptidase P. In yet a further embodiment, a conjugate contains a homing molecule which is a selective inhibitor of aminopeptidase P. In one embodiment, the invention provides a conjugate which contains a moiety linked to a homing molecule that selectively homes to breast vasculature, provided that the homing molecule is not an antibody or antigen-binding fragment thereof.

Where a conjugate contains a homing peptide, the peptide can have, for example, a length of at most 10 or 20 amino acids. If desired, a homing molecule used in a conjugate of the invention can be cyclic. A variety of moieties are useful in a conjugate of the invention including, for example, therapeutic agents, cancer chemotherapeutic agents, pro-apoptotic agents, cytotoxic agents, and detectable labels.

A method or conjugate of the invention relies on a homing molecule that selectively homes to breast vasculature. As used herein, the term "molecule" is used broadly to mean a polymeric or non-polymeric organic chemical such as a small molecule drug; a nucleic acid molecule such as an RNA, a cDNA or an oligonucleotide; a peptide or peptidomimetic; or a protein such as an antibody or a growth factor receptor or a fragment thereof such as an Fv, Fd or Fab fragment of an antibody containing the antigen-binding domain.

Exemplified herein are various homing molecules that selectively home to breast vasculature such as PGPEGAG (SEQ ID NO: 1), CRSS (SEQ ID NO: 3), CRTS (SEQ ID NO: 4), and apstatin and analogs thereof. Additional homing molecules that selectively home to breast vasculature can be identified using in vivo panning, as disclosed in Example I (see, also, U.S. Pat. No. 5,622,699). Molecules that selectively home to breast vasculature further can be identified by contacting aminopeptidase P with one or more molecules, and then determining specific binding of a molecule to aminopeptidase P, as disclosed herein below. In addition, molecules that selectively home to breast vasculature can be identified by contacting aminopeptidase P and PGPEGAG (SEQ ID NO: 1) with one or more molecules, and determining that specific binding of PGPEGAG (SEQ ID NO: 1) to aminopeptidase P was inhibited by at least one of the molecules, as disclosed herein below.

The term "homing molecule," as used herein, means any molecule that selectively homes in vivo to breast vasculature. By "selectively homes" is meant that, in vivo, the homing molecule binds preferentially to breast vasculature as compared to vasculature from a control organ and generally is characterized by at least a two-fold greater localization within breast vasculature as compared to the control vasculature. A homing molecule can be characterized by 5-fold, 10-fold, 20-fold or more preferential localization to breast vasculature as compared to control vasculature. It is understood that a homing molecule can home to one or more other types of vasculature in addition to breast vasculature.

The homing molecules of the invention are provided in isolated form. As used herein in reference to a homing molecule of the invention, the term "isolated" means a molecule that is in a form that is relatively free from material such as contaminating polypeptides, lipids, nucleic acids and other cellular material that normally is associated with the molecule in a cell or that is associated with the molecule in a library.

In one embodiment, a homing molecule of the invention is a peptide or peptidomimetic. The term "peptide" is used broadly herein to mean peptides, proteins, fragments of proteins and the like. In one embodiment, a breast homing peptide of the invention is not an antibody or antigen-binding fragment thereof, which is an art-recognized term that refers to a peptide or polypeptide containing one or more complementarity determining regions (CDRs). See, for example, Borrabaeck, *Antibody Engineering* 2nd Edition, Oxford University Press, New York (1995).

Where a homing molecule that selectively homes to breast vasculature is a peptide, the peptide can have a relatively short length of less than five, six, seven, eight, nine, ten, 12, 15, 20, 25, 30, 35 or 40 amino acids. A homing peptide of the invention also can maintain its homing capability in the context of a significantly longer peptide or polypeptide sequence and can have, for example, a length of up to 50, 100, 150 or 200 amino acids. As disclosed herein, peptides CPGPEGAGC (SEQ ID NO: 2), CRSS (SEQ ID NO: 3) and CRTS (SEQ ID NO: 4) maintained the ability to home when fused to a phage coat protein, confirming that these peptides have homing activity when embedded in larger protein sequences.

In one embodiment, the invention provides chimeric peptides which contain a homing peptide that selectively homes to breast vasculature fused to a second peptide with a separate function. Such chimeric peptides are bifunctional, for example, displaying pro-apoptotic activity in addition to selective homing activity. As exemplary chimeric, bifunctional peptides, the invention provides PGPEGAG-GG-$_D$(KLAKLAK)$_2$, CRSS-GG-$_D$(KLAKLAK)$_2$, and CRTS-GG-$_D$(KLAKLAK)$_2$, which display selective homing activity to breast vasculature in addition to pro-apoptotic activity.

The invention further provides a homing peptide fused to a heterologous protein. In specific embodiments, the invention provides the peptide PGPEGAG (SEQ ID NO: 1), CPGPE-GAGC (SEQ ID NO: 2), CRSS (SEQ ID NO: 3) or CRTS (SEQ ID NO: 4) fused to a heterologous protein, which can have a variety of lengths, for example, up to 100, 200, 400 or 800 amino acid residues. The term "heterologous," as used herein in reference to a protein fused to a homing peptide, means a protein derived from a source other than the gene encoding the homing peptide.

As used herein, the term "peptidomimetic" is used broadly to mean a peptide-like molecule that has the binding activity of the homing peptide upon which it is structurally based. Such peptidomimetics include chemically modified peptides, peptide-like molecules containing non-naturally occurring amino acids, and peptoids and have the selective homing activity of the homing peptide upon which the peptidomimetic is derived (see, for example, Goodman and Ro, *Peptidomimetics for Drug Design*, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α-dialkylglycine or α-aminocycloalkane carboxylic acid; an N$^α$-C$^α$ cylized amino acid; an N$^α$-methylated amino acid; a β- or γ-amino cycloalkane carboxylic acid; an α,β-unsaturated amino acid; a β,β-dimethyl or β-methyl amino acid; a β-substituted-2,3-methano amino acid; an N—C$^δ$ or C$^α$-C$^δ$ cyclized amino acid; a substituted proline or another amino acid mimetic. A peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; transolefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., *Acta Crvstalloqr*. Section B, 35:2331 (1979)). This structural depository is continually updated as new crystal structures are determined and can be screened for compounds having suitable shapes, for example, the same shape as a homing molecule, as well as potential geometrical and chemical complementarity to a target molecule, for example, aminopeptidase P. Where no crystal structure of a homing peptide or a target molecule that binds the homing molecule is available, a structure can be generated using, for example, the program CONCORD (Rusinko et al.,

*J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a homing molecule that selectively homes to breast vasculature.

In one embodiment, a homing molecule of the invention is a cyclic peptide or peptidomimetic. As used herein, the term "cyclic" refers to a peptide or peptidomimetic having an intramolecular bond between two non-adjacent amino acids or amino acid analogues. The cyclization can be effected through a covalent or non-covalent bond. Intramolecular bonds include, but are not limited to, backbone to backbone, side-chain to backbone and side-chain to side-chain bonds. A preferred method of cyclization is through formation of a disulfide bond between the side-chains of non-adjacent amino acids or amino acid analogs. Residues capable of forming a disulfide bond include, for example, cysteine (Cys), penicillamine (Pen), β,β-pentamethylene cysteine (Pmc), β,β-pentamethylene-β-mercaptopropionic acid (Pmp) and functional equivalents thereof (see, also, Table 1).

TABLE 1

AMINO ACIDS AND AMINO ACID ANALOGS USEFUL FOR CYCLIZATION

| AMINO ACID* | THREE LETTER CODE | TYPE OF BOND |
|---|---|---|
| γ-amino-adipic acid | Adp | Lactam |
| Aspartic acid | Asp | Lactam |
| Cysteine | Cys | Disulfide |
| Glutamic acid | Glu | Lactam |
| Leucine | Leu | Lysinonorleucine |
| Lysine | Lys | Lactam and Lysinonorleucine |
| M-(aminomethyl) benzoic acid | Mamb | Lactam |
| Ornithine | Orn | Lactam |
| Penicillamine | Pen | Disulfide |
| α,β-diaminopropionic acid | — | Lactam |
| β,β-pentamethylene cysteine | Pmc | Disulfide |
| β,β-pentamethylene-β-mercaptopropionic acid | Pmp | Disulfide |
| Tyrosine | Tyr | Dityrosine |

*includes amino acids and analogs thereof.

A peptide or peptidomimetic also can cyclize, for example, via a lactam bond, which can utilize a side-chain group of one amino acid or analog thereof to form a covalent attachment to the N-terminal amine of the amino-terminal residue. Residues capable of forming a lactam bond include aspartic acid (Asp), glutamic acid (Glu), lysine (Lys), ornithine (Orn), α,β-diaminopropionic acid, γ-amino-adipic acid (Adp) and M-(aminomethyl)benzoic acid (Mamb). Cyclization additionally can be effected, for example, through the formation of a lysinonorleucine bond between lysine (Lys) and leucine (Leu) residues or a dityrosine bond between two tyrosine (Tyr) residues.

In another embodiment, a homing molecule that selectively homes to breast vasculature is a selective inhibitor of aminopeptidase P. As used herein, the term "selective inhibitor of aminopeptidase P" means an organic molecule that selectively decreases the enzymatic activity of aminopeptidase P. In general, a selective inhibitor of aminopeptidase P is a molecule that binds to the active site of aminopeptidase P. Such an inhibitor can be an organic molecule such as a drug; peptide; modified peptide or peptide mimetic; protein or protein fragment; nucleic acid molecule such as a ribonucleic or deoxyribonucleic acid; oligosaccharide; lipid; glycolipid; or lipoprotein. Exemplary aminopeptidase P inhibitors disclosed herein are apstatin and other apstatin analogs shown in Tables 2 through 4.

TABLE 2

Modifications of the Penultimate Proline or the C-Terminal Residue of Apstatin

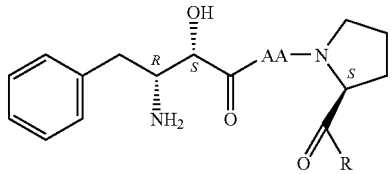

| Compound | AA | R | IC$_{50}$ (µM) for membrane-bound aminopeptidase P$^a$ | | | |
|---|---|---|---|---|---|---|
| | | | human | monkey | rat | bovine |
| 1$^b$ | (pyrrolidine-NH-CH(CH$_3$)-C(O)NH$_2$) | | 2.9 (K$_i$ = 0.64) | 6.1 | 4.1 (K$_i$ = 2.6) | 9.4 (K$_i$ = 7.8) |
| 2 | (thiazolidine-NH-CH(CH$_3$)-C(O)NH$_2$) | | 11. | 18. | 9.2 | 34. |
| 3 | (pyrrolidine) | —NH$_2$ | 79. | 89. | 390. | 1300. |
| 4 | (pyrrolidine) | -ala-β-ala-cys-NH$_2$ (L-amino acids) | 2.8 | 3.4 | 0.66 | 4.0 |

$^a$IC$_{50}$s determined in triplicate by linear regression analysis of the linear portion of the rate vs log inhibitor concentration plot. Average correlation coefficients for all determinations equal to 0.96. IC$_{50}$s determined with 0.5 mM arg = Pro-Pro in 0.1 M Hepes, pH 8.0.
$^b$Compound 1 = apstatin, available from Sigma Chemical Company.

TABLE 3

N-Terminal Modifications of Apstatin
R-Pro-Ala-NH$_2$

| Compound | R | IC$_{50}$ (μM) for membrane-bound aminopeptidase P[a] | | | |
|---|---|---|---|---|---|
| | | human | monkey | rat | bovine |
| 5 | (R,S) isomer with OH, NH$_2$, isobutyl) | 0.23 | 0.13 | 0.56 | 4.5 |
| 6 | (S,R isomer) | 0.43 | 0.23 | 0.31 | 2.1 |
| 7 | (R,R isomer) | 31. | 30. | 19. | 50. |
| 8 | (S,S isomer) | 88. | 58. | 100. | 470 |
| 9 | (phenethyl-CH(COOH)-) | 2.6 | 8.4 | 3.8 (1.5)[b] | 4.6 (1.1)[b] |

[a]IC$_{50}$s determined in triplicate by linear regression analysis of the linear portion of the rate vs log inhibitor concentration plot. Average correlation coefficients for all determinations equal to 0.96. IC$_{50}$s determined with 0.5 mM arg = Pro-Pro in 0.1 M Hepes, pH 8.0.
[b]In the presence of mM MnCl$_2$.

TABLE 4

Substitutions for the AHPB-Pro Residues of Apstatin
R-Pro-Ala-NH$_2$

| Compound | R | stereoisomer | IC$_{50}$ (μM) for membrane-bound aminopeptidase P[a] | | | |
|---|---|---|---|---|---|---|
| | | | human | monkey | rat | bovine |
| 10 | (2-mercaptocyclopentanecarbonyl) | trans (?) fast isomer[b] | 29 | 13. | 3.4 | 10. |
| 11 | (2-mercaptocyclopentanecarbonyl) | cis(?) slow isomer[b] | 390. | 300. | 150. | 300. |

TABLE 4-continued

Substitutions for the AHPB-Pro Residues of Apstatin
R-Pro-Ala-NH₂

| Compound | R | stereoisomer | IC$_{50}$ (µM) for membrane-bound aminopeptidase P[a] | | | |
|---|---|---|---|---|---|---|
| | | | human | monkey | rat | bovine |
| 12 | 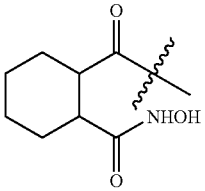 | trans fast isomer[b] | 48. | 21. | 37. | 50. |

[a]IC$_{50}$s determined in triplicate by linear regression analysis of the linear portion of the rate vs log inhibitor concentration plot. Average correlation coefficients for all determinations equal to 0.96.
IC$_{50}$s determined with 0.5 mM arg = Pro-Pro in 0.1 M Hepes, pH 8.0.
[b]Fast and slow moving isomers from reverse phase HPLC.

A variety of selective inhibitors of aminopeptidase P are known in the art or can be identified by routine methods described herein below. Such selective inhibitors of aminopeptidase P include apstatin and are described, for example, in Maggiora, supra, 1999, and Stockel et al., "Specific Inhibitors of Aminopeptidase P," in Ansorge and Langner (Eds), *Cellular Peptidases in Immune Functions and Diseases* Plenum Press, New York 1997.

The conjugates of the invention are useful in preventing, treating or reducing the severity of breast cancer, including various stages of breast cancer. In one embodiment, a conjugate of the invention is administered to a woman at high risk of developing breast cancer to reduce the amount of breast tissue. Such a conjugate can contain, for example, a homing molecule that selectively homes to breast vasculature linked to a moiety such as a cytotoxic or pro-apoptotic moiety, wherein, upon administration to a subject, there is selective ablation of breast tissue. In another embodiment, a conjugate of the invention is administered to a subject having pre-malignant breast tissue. In a further embodiment, a conjugate of the invention is administered to a subject having early breast cancer.

The conjugates of the invention include a moiety linked to a homing molecule that selectively homes to breast vasculature. As used herein, the term "moiety" is used broadly to mean a physical, chemical, or biological material that can be linked to a breast homing molecule of the invention and generally imparts a biologically useful function to the breast homing molecule. A moiety can be any natural or nonnatural material including an organic chemical such as a small molecule, radionuclide, nucleic acid molecule or oligonucleotide, polypeptide, peptide or peptidomimetic. A moiety can be, for example, a therapeutic agent; cancer chemotherapeutic agent, pro-apoptotic agent, cytotoxic agent, diagnostic label or imaging agent; or a tag or insoluble support. These and other moieties known in the art can be components of a conjugate of the invention, as disclosed herein below.

In one embodiment, a moiety is a therapeutic agent. As used herein, the term "therapeutic agent" means a molecule with a clinically valuable biological activity in a normal or pathologic tissue. A variety of therapeutic agents can be useful in a conjugate of the invention. A therapeutic agent useful for treating breast cancer can be, for example, a taxane such as docetaxel; an anthracyclin such as doxorubicin; an alkylating agent; a vinca alkaloid; an anti-metabolite; a platinum agent; a selective estrogen receptor modulator; a therapeutic antibody such as trastuzumab; or another agent useful for preventing, treating or reducing the severity of breast cancer.

A therapeutic agent useful in a conjugate of the invention can be, for example, a taxane drug such as docetaxel (Taxotere; Aventis Pharmaceuticals, Inc.; Parsippany, N.J.) or paclitaxel (Taxol; Bristol-Myers Squibb; Princeton, N.J.). See, for example, Chan et al., *J. Clin. Oncol.* 17:2341-2354 (1999), and Paridaens et al., *J. Clin. Oncol.* 18:724 (2000). Doxetaxel can be used in a conjugate of the invention, for example, for treatment of anthracyclin-resistant breast cancer (Burris, *Seminars in Oncol.* 28:38-44 (2001)).

A therapeutic agent useful in a conjugate of the invention also can be an anthracyclin such as doxorubicin, idarubicin or daunorubicin. Doxorubicin is a commonly used cancer chemotherapeutic agent and, particularly, can be useful for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, supra, 1997; Steiner, In "Angiogenesis: Key principles-Science, technology and medicine," pp. 449-454 (eds. Steiner et al.; Birkhauser Verlag, 1992)), which can contribute to its effectiveness in treating cancer.

In addition to an anthracyclin, an alkylating agent such as melphalan or chlorambucil can be a therapeutic agent useful in a conjugate of the invention. Similarly, a vinca alkaloid such as vindesine, vinblastine or vinorelbine; or an antimetabolite such as 5-fluorouracil, 5-fluorouridine or a derivative thereof also is a cancer chemotherapeutic agent useful when conjugated to a breast homing molecule. Other chemotherapeutic agents useful in a conjugate of the invention include cis-platinum, methotrexate, and mitomycin-C.

A therapeutic agent for treatment of breast cancer also can be an agent that antagonizes the effect of estrogen, such as a selective estrogen receptor modulator or an anti-estrogen. The selective estrogen receptor modulator, tamoxifen, is a therapeutic agent that can be used in a conjugate of the invention for treatment of breast cancer (Fisher et al., *J. Natl. Cancer Instit.* 90:1371-1388 (1998)).

A therapeutic agent to be linked to a breast homing molecule in a conjugate of the invention also can be a platinum agent. Such a platinum agent can be, for example, cisplatin or carboplatin as described, for example, in Crown, *Seminars in Oncol.* 28:28-37 (2001).

A therapeutic agent useful in a conjugate of the invention also can be an antibody such as a humanized monoclonal antibody. For example, the anti-epidermal growth factor receptor 2 (HER2) antibody, trastuzumab (Herceptin; Genentech, South San Francisco, Calif.) is a therapeutic agent useful in a conjugate of the invention for treating HER2/neu overexpressing breast cancers (Burris et al., supra, 2001; White et al., *Annu. Rev. Med.* 52:125-141 (2001)).

In one embodiment, a conjugate of the invention contains a cytotoxic agent linked to a homing molecule that selectively homes to breast vasculature. As used herein, the term "cytotoxic agent" refers to any molecule that results in cell death by any mechanism. Exemplary cytotoxic agents are doxorubicin, docetaxel and trastuzumab and antimicrobial peptides, described herein below.

The invention further provides a conjugate in which a homing molecule that selectively homes to a breast vasculature is linked to an antimicrobial peptide, where the conjugate is selectively internalized by breast tissue and exhibits a high toxicity to the breast tissue, and where the antimicrobial peptide has low mammalian cell toxicity when not linked to the homing molecule. As used herein, the term "antimicrobial peptide" means a naturally occurring or synthetic peptide having antimicrobial activity, which is the ability to kill or slow the growth of one or more microbes and which has low mammalian cell toxicity when not linked to a homing molecule. An antimicrobial peptide can, for example, kill or slow the growth of one or more strains of bacteria including a Gram-positive or Gram-negative bacteria, or a fungi or protozoa. Thus, an antimicrobial peptide can have, for example, bacteriostatic or bacteriocidal activity against, for example, one or more strains of *Escherichia coli, Pseudomonas aeruginosa* or *Staphylococcus aureus*. While not wishing to be bound by the following, an antimicrobial peptide can have biological activity due to the ability to form ion channels through membrane bilayers as a consequence of self-aggregation.

An antimicrobial peptide is typically highly basic and can have a linear or cyclic structure. As discussed further below, an antimicrobial peptide can have an amphipathic α-helical structure (see U.S. Pat. No. 5,789,542; Javadpour et al., supra, 1996; Blondelle and Houghten, supra, 1992). An antimicrobial peptide also can be, for example, a β-strand/sheet-forming peptide as described in Mancheno et al., *J. Peptide Res.* 51:142-148 (1998).

An antimicrobial peptide can be a naturally occurring or synthetic peptide. Naturally occurring antimicrobial peptides have been isolated from biological sources such as bacteria, insects, amphibians and mammals and are thought to represent inducible defense proteins that can protect the host organism from bacterial infection. Naturally occurring antimicrobial peptides include the gramicidins, magainins, mellitins, defensins and cecropins (see, for example, Maloy and Kari, *Biopolymers* 37:105-122 (1995); Alvarez-Bravo et al., *Biochem. J.* 302:535-538 (1994); Bessalle et al., *FEBS* 274: 151-155 (1990); and Blondelle and Houghten in Bristol (Ed.), *Annual Reports in Medicinal Chemistry* pages 159-168 Academic Press, San Diego). As discussed further below, an antimicrobial peptide also can be an analog of a natural peptide, especially one that retains or enhances amphipathicity.

An antimicrobial peptide incorporated within a conjugate of the invention has low mammalian cell toxicity when not linked to a breast homing molecule. Mammalian cell toxicity readily can be assessed using routine assays. For example, mammalian cell toxicity can be assayed by lysis of human erythrocytes in vitro as described in Javadpour et al., supra, 1996. An antimicrobial peptide having low mammalian cell toxicity is not lytic to human erythrocytes or requires concentrations of greater than 100 µM for lytic activity, preferably concentrations greater than 200, 300, 500 or 1000 µM.

In one embodiment, the invention provides a conjugate in which the antimicrobial peptide portion promotes disruption of mitochondrial membranes when internalized by eukaryotic cells. In particular, such an antimicrobial peptide preferentially disrupts mitochondrial membranes as compared to eukaryotic membranes. Mitochondrial membranes, like bacterial membranes but in contrast to eukaryotic plasma membranes, have a high content of negatively charged phospholipids. An antimicrobial peptide can be assayed for activity in disrupting mitochondrial membranes using, for example, an assay for mitochondrial swelling (as described in Example I) or another assay well known in the art. As disclosed herein, for example, $_D$(KLAKLAK)$_2$ induced marked mitochondrial swelling at a concentration of 10 µM, significantly less than the concentration required to kill eukaryotic cells. An antimicrobial peptide that induces significant mitochondrial swelling at, for example, 50 µM, 40 µM, 30 µM, 20 µM, 10 µM, or less, is considered a peptide that promotes disruption of mitochondrial membranes.

An antimicrobial peptide portion can include, for example, the sequence (KLAKLAK)$_2$ (SEQ ID NO: 16), (KLAKKLA)$_2$ (SEQ ID NO: 17), (KAAKKAA)$_2$ (SEQ ID NO: 18), or (KLGKKLG)$_3$ (SEQ ID NO: 19), and, in one embodiment, includes the sequence $_D$(KLAKLAK)$_2$. A conjugate of the invention, which contains a homing molecule that selectively homes to breast vasculature linked to an antimicrobial peptide, can have, for example, the sequence PGPEGAG-GG-$_D$(KLAKLAK)$_2$, CRSS-GG-$_D$(KLAKLAK)$_2$, or CRTS-GG-$D$(KLAKLAK)$_2$.

Antimicrobial peptides generally have random coil conformations in dilute aqueous solutions, yet high levels of helicity can be induced by helix-promoting solvents and amphipathic media such as micelles, synthetic bilayers or cell membranes. α-Helical structures are well known in the art, with an ideal α-helix characterized by having 3.6 residues per turn and a translation of 1.5 Å per residue (5.4 Å per turn; see Creighton, *Proteins: Structures and Molecular Properties* W. H Freeman, New York (1984)). In an amphipathic α-helical structure, polar and non-polar amino acid residues are aligned into an amphipathic helix, which is an α-helix in which the hydrophobic amino acid residues are predominantly on one face, with hydrophilic residues predominantly on the opposite face when the peptide is viewed along the helical axis.

Antimicrobial peptides of widely varying sequence have been isolated, sharing an amphipathic α-helical structure as a common feature (Saberwal et al., *Biochim. Biophys. Acta* 1197:109-131 (1994)). Analogs of native peptides with amino acid substitutions predicted to enhance amphipathicity and helicity typically have increased antimicrobial activity. In general, analogs with increased antimicrobial activity also have increased cytotoxicity against mammalian cells (Maloy et al., *Biopolymers* 37:105-122 (1995)).

As used herein in reference to an antimicrobial peptide, the term amphipathic α-helical structure means an α-helix with a hydrophilic face containing several polar residues at physiological pH and a hydrophobic face containing nonpolar residues. A polar residue can be, for example, a lysine or arginine residue, while a nonpolar residue can be, for example, a leucine or alanine residue. An antimicrobial peptide having an amphipathic α-helical structure generally has an equivalent number of polar and nonpolar residues within the amphipathic domain and a sufficient number of basic residues to give the peptide an overall positive charge at neutral pH (Saberwal et al., *Biochim. Biophys. Acta* 1197:109-131 (1994)). One skilled in the art understands that helix-promoting amino acids such as leucine and alanine can be advantageously included in an antimicrobial peptide of the invention (see, for example, Creighton, supra, 1984). Synthetic, antimicrobial peptides having an amphipathic α-helical structure are known in the art, for example, as described in U.S. Pat. No. 5,789,542 to McLaughlin and Becker.

A therapeutic agent useful in a conjugate of the invention also can be an anti-angiogenic agent, which is a molecule that reduces or prevents angiogenesis. Vascular endothelial growth factor (VEGF) has been shown to be important for breast cancer angiogenesis in vivo (Borgstrom et al., *Anticancer Res.* 19:4213-4214 (1999)). An anti-angiogenic agent can be, for example, an inhibitor or neutralizing antibody that inhibits a growth factor or other factor important for angiogenesis. In one embodiment, the anti-angiogenic agent is an anti-VEGF neutralizing monoclonal antibody (Borgstrom et al., supra, 1999).

It is understood by one skilled in the art of medicinal oncology that these and other agents are useful therapeutic agents, which can be used separately or together in treating breast cancer. It further is understood that a conjugate of the invention can contain one or more of such therapeutic agents and that additional components can be included as part of the conjugate, if desired. For example, in some cases, it can be desirable to utilize an oligopeptide spacer between the homing molecule and the therapeutic agent (Fitzpatrick and Garnett, *Anticancer Drug Des.* 10:1-9 (1995)).

Further provided by the invention is a method of imaging breast vasculature in a subject. The method includes the steps of administering to the subject a conjugate containing a detectable label linked to a molecule that specifically binds aminopeptidase P, whereby the conjugate specifically binds breast vasculature; and detecting the conjugate. In a method of the invention for imaging breast vasculature, the homing molecule can be, for example, a peptide or peptidomimetic, such as a peptide comprising the amino acid sequence PGPEGAG (SEQ ID NO: 1), or a peptidomimetic thereof, and, if desired, can be a cyclic peptide or peptidomimetic. A homing peptide useful in the invention, such as a peptide including the amino acid sequence PGPEGAG (SEQ ID NO: 1), can have a length of, for example, at most 10 or 20 amino acids. In one embodiment, the homing molecule that specifically binds aminopeptidase P is a selective inhibitor of aminopeptidase P. A variety of detectable labels are useful in the imaging methods of the invention, including, for example, indium-111, technitium-99, carbon-11 and carbon-13.

The imaging methods of the invention can be useful for detecting the presence or absence of pathology in the breast. For example, following administration of a breast homing molecule conjugated to a detectable label, breast vasculature can be visualized. If the image is abnormal, for example, if the local distribution of breast vasculature is other than that expected for a size and age matched subject, the imaging result can indicate the presence of cancer.

In a method of imaging breast vasculature, the conjugate administered contains a detectable label that allows detection or visualization of breast vasculature. For in vivo diagnostic imaging of breast vasculature, a breast homing molecule is linked to a detectable label that, upon administration to the subject, is detectable external to the subject. Such a detectable label can be, for example, a gamma ray emitting radionuclide such as indium-113, indium-115 or technetium-99; following administration to a subject, the conjugate can be visualized using a solid scintillation detector.

The present invention is directed to the surprising discovery that aminopeptidase P-binding molecules home specifically to breast vasculature in spite of aminopeptidase p expression in other tissues such as kidney and lung. As disclosed herein, phage bearing aminopeptidase P-binding peptide SEQ ID NO: 1 homed selectively to breast vasculature in preference to pancreas, brain, kidney, lung and skin and in spite of the fact that aminopeptidase P is expressed in lung vasculature. These results indicate that aminopeptidase P can act as a receptor to mediate selective homing of molecules to breast vasculature in preference to the vasculature in other organs.

Based on this finding, the present invention provides a method of identifying a homing molecule that selectively homes to breast vasculature by contacting aminopeptidase P with one or more molecules; and determining specific binding of a molecule to aminopeptidase P, where the presence of specific binding identifies at least one of the molecules as a homing molecule that selectively homes to breast vasculature. A method of the invention for identifying a homing molecule that selectively homes to breast vasculature can be practiced, for example, with substantially purified aminopeptidase P. In one embodiment, the invention is practiced with aminopeptidase P immobilized on a support. In another embodiment, the invention is practiced with human aminopeptidase P.

The present invention also provides a method of identifying a homing molecule that selectively homes to breast vasculature by contacting aminopeptidase P and a peptide containing the amino acid sequence PGPEGAG (SEQ ID NO: 1), or a peptidomimetic thereof, with one or more molecules; and determining specific binding of the peptide or peptidomimetic to aminopeptidase P in the presence of the one or more molecules as compared to binding in the absence of the one or more molecules, where inhibition of specific binding identifies at least one of the molecules as a homing molecule that selectively homes to breast vasculature. In a method of the invention, the aminopeptidase P can be, for example, substantially purified. In one embodiment, the aminopeptidase P is human aminopeptidase P.

Further provided by the invention is a method of identifying a homing molecule that selectively homes to breast vasculature by contacting aminopeptidase P with one or more molecules; and determining selective inhibition of aminopeptidase P by at least one of the molecules, where the presence of selective inhibition identifies at least one of the molecules as a homing molecule that selectively homes to breast vasculature. The aminopeptidase P can be, for example, substantially purified aminopeptidase P. In one embodiment, the aminopeptidase P is immobilized on a support. In another embodiment, the aminopeptidase P is human aminopeptidase P.

The methods of the invention for identifying a homing molecule that selectively homes to breast vasculature can be practiced in vivo or in vitro, and aminopeptidase P can be obtained from a number of sources. Sources of aminopeptidase P include whole cells or cell extracts containing endogenous or exogenous aminopeptidase P. Sources of endogenous aminopeptidase P include, for example, breast tissue, breast vasculature, or breast endothelial cell lines. Sources of aminopeptidase P further include partially purified cell extracts; biochemically purified enzyme, for example, affinity purified aminopeptidase P; recombinant polypeptide; and transfected cell lines, which can be, for example, endothelial cell lines such as breast endothelial cell lines.

Aminopeptidase P (AP-P; E.C. 3.4.11.9; X-Pro aminopeptidase) is expressed in a variety of different organisms, including mammals, yeast and bacteria, and is one of the rare enzymes which process proline motifs in peptides. This exopeptidase cleaves the N-terminal residue from long and short peptides with a penultimate proline and is one of only a few proline specific peptidases that can cleave the imide bond on the amino-terminal side of proline. Physiological substrates for aminopeptidase P include bradykinin, which has potent vasodilatory and cardioprotective effects; this substrate is inactivated, in part, through cleavage by aminopeptidase P (Lloyd et al., *Biochem. Pharmacol.* 52:229-236 (1996).

Specificity studies with aminopeptidase P have revealed a broad specificity for the first amino acid of a peptide substrate, while proline or hydroxyproline is generally seen in the second position. Dipeptides are not cleaved by aminopeptidase P, and the third amino acid typically has a small side chain, for example, alanine, proline, glycine, or valine. In addition, aminopeptidase P generally shows higher binding affinities for tetrapeptide than tripeptide substrates (Simmons and Orawski, *J. Biol. Chem.* 267:4897-4903 (1992); Yoshimoto et al., *Arch. Biochem. Biophys.* 311:28-34 (1994); and Orawski and Simmons, Biochemistry 34:11227-11236 (1995)). Aminopeptidase P can be selectively inhibited by apstatin with a Ki value of 2.6 µM and 0.64 µM for rat and human membrane-bound aminopeptidase P, respectively (Yoshimoto et al., supra, 1994).

Aminopeptidase P is known to occur in two forms: a membrane-bound form and a cytosolic form (Dehm and Nordwig, *Eur. J. Biochem.* 17:364-371 (1970)). The membrane-bound form, first purified from porcine kidney, is attached to the lipid bilayer by a glycosyl-phosphatidylinositol (GPI) anchor (Hooper et al., *Biochem. J.* 267:509-515 (1990)). The membrane-bound form of aminopeptidase P is located as an ectoenzyme on the plasma membrane of endothelial and epithelial cells. GPI anchors membrane-bound aminopeptidase P to the luminal surface of the pulmonary microvascular endothelium (Ryan et al., *Immunopharmacol.* 32:149-152 (1996)). The cDNA encoding membrane-bound aminopeptidase P encodes a protein with a cleavable N-terminal signal peptide that directs translocation into the endoplasmic reticulum, and a C-terminal GPI anchor attachment signal (Hyde et al., *Biochem. J.* 319:197-201 (1996)).

Aminopeptidase P has been purified from a variety of sources. The soluble form of aminopeptidase P has been purified, for example, from human platelets (van Hoof et al., *Biochem. Pharmacol.* 44:479-487 (1992)), human leukocytes (Rusu and Yaron, *Eur. J. Biochem.* 210:93-100 (1992)), rat brain (Harbeck and Mentlein, *Eur. J. Biochem.* 198: 451-458 (1991)), and guinea pig serum (Ryan et al., *Biochim. Biophys. Acta* 1119:140-147 (1992); and Ryan et al., *Biochem. Biophys. Res. Comm.* 205:1796-1802 (1994)). The insoluble, membrane-bound form of aminopeptidase P has been purified, for example, from pig kidney (Hooper et al., *Biochem. J.* 267:509-515 (1990); Romero et al., *Eur. J. Biochem.* 229:262-269 (1995), bovine lung (Simmons and Orawski, *J. Biol. Chem.* 267:4897-4903 (1992), rat lung (Orawski and Simmons, *Biochemistry* 34:11227-11236 (1995) and guinea pig lung and kidney (Ryan et al., supra, 1994). The membrane-bound form of aminopeptidase P is heavily glycosylated and, as discussed above, contains a GPI anchor.

The human membrane-bound aminopeptidase P cDNA has an open reading frame of 2019 nucleotides and a deduced amino acid sequence of 673 residues with a calculated molecular weight of about 75 kDa (Venema et al., *Biochimica et Biophysica Acta* 1354:45-48 (1997)). Comparison of the human aminopeptidase P amino acid sequence to that of porcine aminopeptidase P reveals 83% amino acid identity between the two species. Human membrane-bound aminopeptidase P is widely expressed as determined by Northern analysis, with expression detected in kidney, lung, heart, placenta, liver, small intestine and colon while no expression was observed in brain., skeletal muscle, pancreas, spleen, thymus, prostate, testis, ovary and leukocytes (Venema et al., supra, 1997).

As used herein, the term "aminopeptidase P" is synonymous with "X-Pro aminopeptidase," "APP" and "AP-P" and means an enzyme that cleaves the imide bond on the amino-terminal side of proline and which is selectively inhibited by apstatin. The term aminopeptidase P encompasses any bacterial, yeast or mammalian aminopeptidase P, for example, a human, monkey, bovine, porcine, guinea pig, rat, murine or *E. coli* homolog of aminopeptidase P. An exemplary human membrane-bound aminopeptidase P sequence is provided herein as SEQ ID NO: 8 in FIG. 7 (see, also, GenBank accession U90724). The term aminopeptidase P includes any homolog of human aminopeptidase P as well as any related polypeptide having substantial amino acid sequence similarity to an aminopeptidase P homolog. Such related polypeptides generally will exhibit greater sequence similarity to SEQ ID NO: 8 than to other proline directed peptidases and include membrane-bound and cytosolic forms of aminopeptidase P, alternatively spliced forms and isotype variants of the human aminopeptidase P amino acid sequence shown in FIG. 7 and other species homologs known in the art. Thus, the term aminopeptidase P encompasses homologous polypeptides obtained from different species as well as other variants and related polypeptides that generally have amino acid identities of greater than 50% with SEQ ID NO: 8, and can have amino acid identities of greater than 60%, 70%, 80%, 90% or 95% with SEQ ID NO: 8. It is understood that the term aminopeptidase P encompasses mature forms of the protein lacking signal peptides, for example, mature forms of human aminopeptidase P beginning at Lys-24 or His-22 as shown in FIG. 7.

It further is clear to the skilled person that the term aminopeptidase P encompasses polypeptides with one or more naturally occurring or non-naturally occurring amino acid substitutions, deletions or insertions as compared to SEQ ID NO: 8, provided that the polypeptide retains enzymatic activity. Modifications to naturally occurring aminopeptidase P polypeptides that are encompassed within the definition of aminopeptidase P include, for example, an addition, deletion, or substitution of one or more conservative or non-conservative amino acid residues; substitution of a compound that mimics amino acid structure or function; or addition of chemical moieties such as amino or acetyl groups. The activity of a modified aminopeptidase P or fragment thereof can be assayed using an appropriate substrate such as Arg-Pro-Pro as described in Simmons and Orawski, supra, 1992.

It is understood that one skilled in the art can identify a homing molecule that selectively homes to vasculature using any aminopeptidase P, including naturally and non-naturally occurring forms of the enzyme. In one embodiment, a method of the invention for identifying breast homing molecules is practiced with a membrane-bound aminopeptidase P. In another embodiment, a method of the invention relies on a mammalian aminopeptidase P. In a further embodiment, identification of breast homing molecules according to a method of the invention uses a mammalian membrane-bound aminopeptidase P, which can be, for example, a human membrane aminopeptidase P (see FIG. 7).

It further is understood that a method for identifying a homing molecule that selectively homes to breast vasculature can be practiced with an active fragment of aminopeptidase P. As used herein, the term "active fragment" means a polypeptide fragment that has substantially the amino acid sequence of a portion of an aminopeptidase P polypeptide and that retains the enzymatic activity of the parent polypeptide. An active fragment of aminopeptidase P can have, for example, substantially the amino acid sequence of the carboxy-terminal half of a mammalian aminopeptidase P such as the carboxy-terminal half of human membrane-bound aminopeptidase P. See, for example, Cottrell et al., *Biochemistry* 39:15129-15135 (2000), in which residues involved in metal binding and catalysis were identified.

In one embodiment, a method of the invention for identifying a homing molecule that selectively homes to breast vasculature is practiced with substantially purified aminopeptidase P. The term "substantially purified," as used herein in reference to an aminopeptidase P polypeptide or active fragment thereof, means that the polypeptide or active fragment is in a form that is relatively free from contaminating lipids, nucleic acids, unrelated polypeptides and other cellular material normally associated with aminopeptidase P in a cell.

Affinity chromatography can be particularly useful for purifying or partially purifying aminopeptidase P for use in identifying a homing molecule according to a method of the invention. For example, aminopeptidase P can be purified from breast tissue extracts, breast vasculature, a breast endothelial cell line, or another cell line or tissue in which aminopeptidase P is expressed by affinity chromatography using immobilized peptide CPGPEGAGC (SEQ ID NO: 2) as described in Example III. Similarly, aminopeptidase P can be obtained by affinity chromatography using other immobilized ligands such as apstatin. A partially purified preparation of membrane-bound aminopeptidase P can be readily obtained, for example, by treatment of cultured cells or cells from dispersed tissue with phosphatidylinositol-specific phospholipase C (ICN; Costa Mesa, Calif.), followed by centrifugation as described previously in Simmons and Orawski, supra, 1992.

Recombinant aminopeptidase P or an active fragment thereof also can be useful for identifying a breast homing molecule according to a method of the invention. The amino acid and nucleic acid sequences of a variety of aminopeptidase P homologs are known in the art. Nucleic acid sequences encoding an aminopeptidase P can be obtained, for example, from the literature or from databases such as GenBank. See, for example, the membrane-bound human aminopeptidase P sequence available as GenBank accession U90724; the membrane-bound porcine aminopeptidase P sequence available as GenBank accession U55039; the murine membrane-bound aminopeptidase P sequence available as GenBank accession AF367247; the rat membrane-bound aminopeptidase P sequence available as GenBank accession AF359355; the human cytosolic aminopeptidase P sequence available as GenBank accession AF272981; the murine cytosolic aminopeptidase P sequence available as GenBank accession AF363970; and the *E. coli* aminopeptidase P sequence available as GenBank accession P15034. Novel aminopeptidase P cDNAs can be isolated from additional mammalian species with a nucleotide sequence as a probe or primer using methods well known in the art of molecular biology (Innis et al. (Ed.), *PCR Protocols*, San Diego: Academic Press, Inc. (1990)). One skilled in the art knows a variety of methods for expression of aminopeptidase P encoding nucleic acids and subsequent isolation of recombinant aminopeptidase P polypeptide.

In the methods of the invention for identifying a homing molecule that selectively homes to breast vasculature, specific binding of a molecule to aminopeptidase P can identify the molecule as a homing molecule that selectively homes to breast vasculature. The term "specific binding," as used herein in reference to a molecule and aminopeptidase P, means that the molecule has an affinity for aminopeptidase P that is measurably different from a non-specific interaction. Specific binding can be measured, for example, by determining binding of a molecule compared to binding of a control molecule, which generally is a molecule of similar structure that does not have binding activity. In this case, specific binding is indicated if the molecule has measurably higher affinity for aminopeptidase P than the control molecule. Specificity of binding also can be determined, for example, by competition with a control molecule that is known to bind to aminopeptidase P, for example, a peptide containing the PGPEGAG (SEQ ID NO: 1) motif.

The term specific binding, as used herein, includes both low and high affinity specific binding. Specific binding can be exhibited, for example, by a low affinity aminopeptidase P-binding molecule having a Kd for aminopeptidase P of about $10^{-4}$ M to about $10^{-7}$ M. Specific binding also can be exhibited by a high affinity aminopeptidase P binding molecule, for example, an aminopeptidase P-binding molecule having a Kd for aminopeptidase P of at least about $10^{-7}$ M, at least about $10^{-8}$ M, at least about $10^{-9}$ M, at least about $10^{-10}$ M, or at least about $10^{-11}$ M or $10^{-12}$ M. Both low and high affinity aminopeptidase P-binding molecules can be useful as homing molecules to selectively direct a moiety to breast vasculature in a subject as disclosed herein.

A molecule that specifically binds aminopeptidase P binds in preference to an unrelated protein such as albumin or in preference to a related but distinct enzyme, for example, in preference to one or all other proline-directed peptidases. In one embodiment, a molecule that specifically binds aminopeptidase P has little or no binding to other proline-directed peptidases such as prolidase.

A variety of art known techniques can be used to determine specific binding of a molecule to aminopeptidase P according to a method of the invention. Conditions suitable for specific binding are described, for example, in Example III. Specific binding can be determined by transfecting cells lacking aminopeptidase P expression with an aminopeptidase P-encoding nucleic acid molecule. In this case, specific binding can be determined by significantly higher binding of a molecule to the aminopeptidase P-transfected cells than to untransfected cells. Homing molecules that selectively home to breast vasculature also can be identified by selecting molecules which inhibit binding of a known aminopeptidase P binding molecule such as a peptide containing the amino acid sequence PGPEGAG (SEQ ID NO: 1), or a peptidomimetic thereof, to aminopeptidase P.

The term "selective inhibition," as used herein in reference to a aminopeptidase P, means a decrease in aminopeptidase P enzymatic activity in a manner that is selective for the aminopeptidase P enzyme as compared to related but different enzymes such as other proteases. Thus, selective inhibition of aminopeptidase P is distinct from non-specific inhibition of, for example, all zinc metalloproteases. In one embodiment, selective inhibition is a decrease in aminopeptidase P enzymatic activity as compared to one or all other proline-directed peptidases. For example, a molecule that selectively inhibits aminopeptidase P can selectively decrease aminopeptidase P activity while having little or no effect on the activity of other proline-directed peptidases such as prolidase.

A variety of assays are known in the art for determining enzymatic activity of aminopeptidase P. All forms of aminopeptidase P can be routinely assayed, for example, using 0.5 mM Arg-Pro-Pro (Bachem Biosciences; Philadelphia, Pa.) in 0.1 M Hepes, pH 8.0. The enzyme reaction can be followed by measuring the increase in production of free arginine by a fluorescence assay, as described, for example, in Simmons and Orawski, supra, 1992 (see, also, Maggiora et al., *J. Med. Chem.* 42:2394-2402 (1999). Additional fluorogenic substrates for conveniently assaying for selective inhibition of aminopeptidase P are known in the art, as described, for example, in Hawthorne et al., *Analytical Biochem.* 253: 13-17 (1997). One skilled in the art understands that these and other routine assays can be used in the methods of the invention.

The following examples are intended to illustrate but not limit the present invention.

EXAMPLE I

The Cyclic Peptide CPGPEGAGC (SEQ ID NO: 2) Homes to Breast Tissue

This example demonstrates that in vivo panning can be used to identify a peptide that selectively homes to breast tissue.

Figure 1:
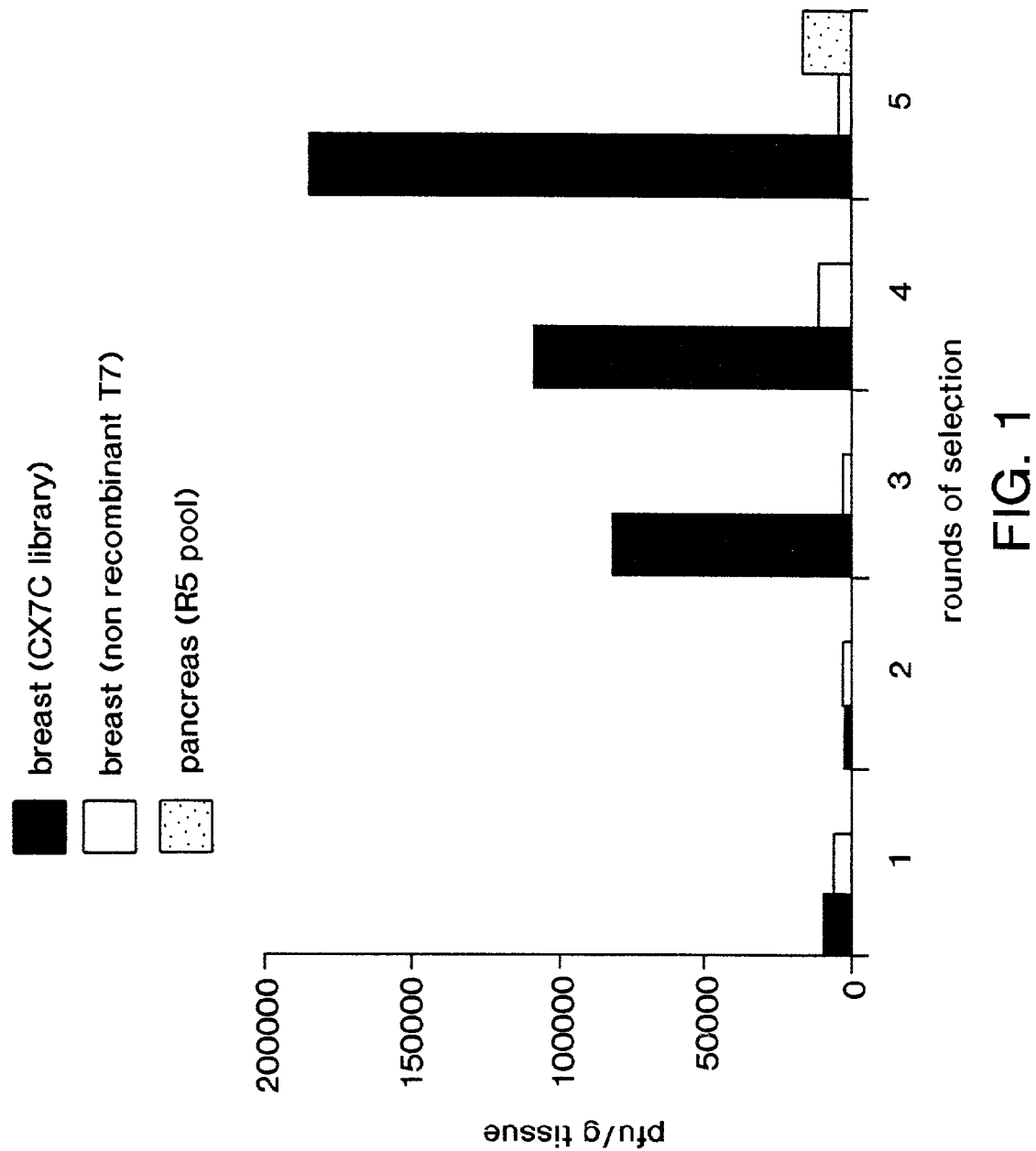
FIG. 1 shows isolation of a breast-targeting phage by in vivo screening of a phage library. A $CX_7C$ library ($10^9$ plaque forming units) was injected into the tail vein of mice; after seven minutes, the mice were perfused through the heart, and phage rescued from breast tissue. The rescued phage were then amplified and re-injected in four additional consecutive rounds. The number of plaque forming units (pfu) recovered from breast tissue is shown (black bars). As a control, non-recombinant T7 phage were injected (white bars). In round five, the number of pfu of phage recovered from the pancreas also was determined (gray bar).

Phage that home selectively to mammary vasculature were identified by intravenous injection of a phage library into mice and subsequently rescue of the phage from breast tissue. FIG. 1 shows the enrichment profile obtained in 5 rounds of phage selection. The number of phage recovered from breast tissue increased to about 100-fold in five rounds of selection. The number of phage recovered from the pancreas, which was used as a control tissue, remained unaffected. Non-recombinant T7 phage were not enriched by in vivo selection for breast homing.

Figure 2:
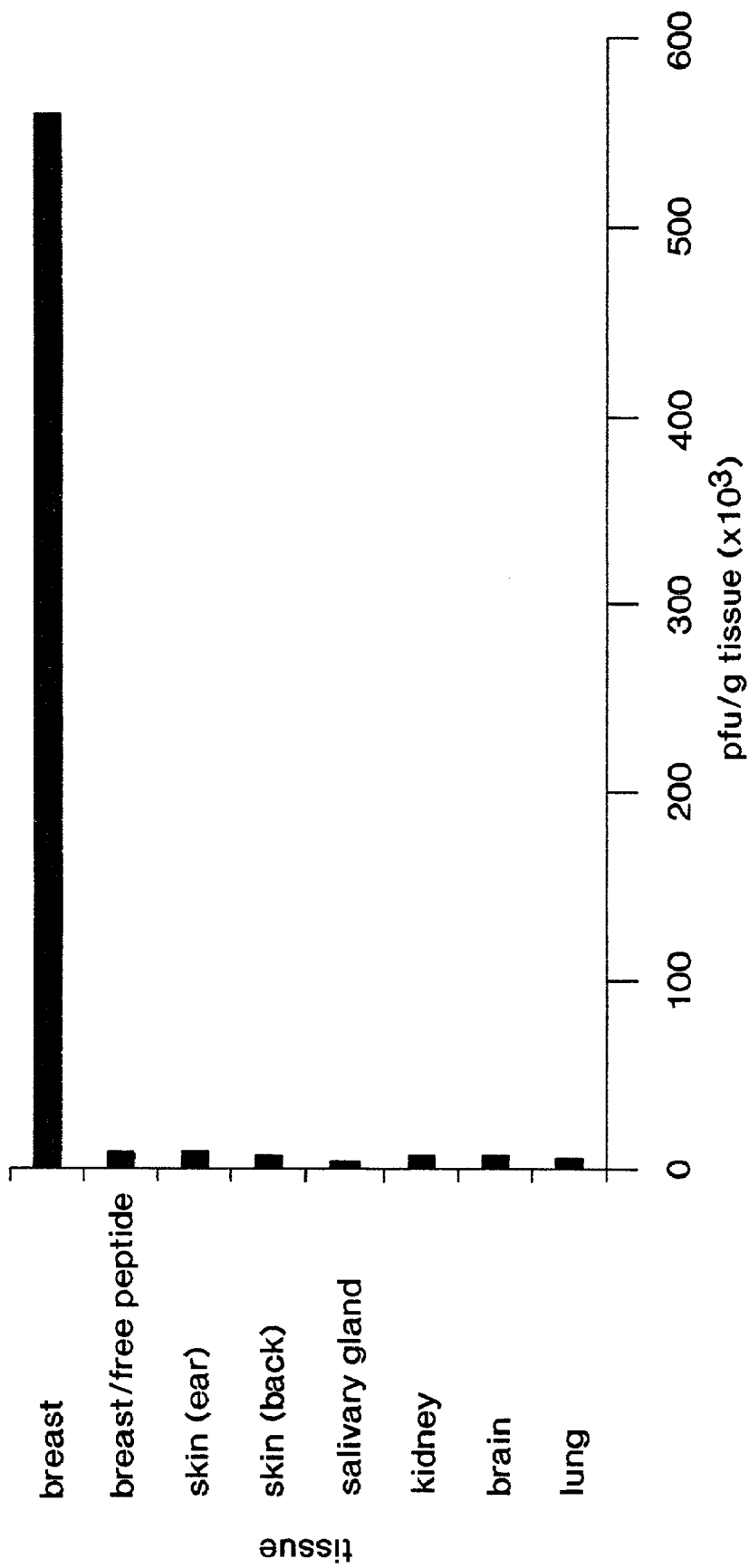
FIG. 2 shows recovery of CPGPEGAGC (SEQ ID NO: 2) phage from a variety of tissues. CPGPEGAGC (SEQ ID NO: 2) phage ($10^9$ pfu) were injected into mice, and phage recovered from the indicated organs. The number of pfu recovered from each organ is shown. "Breast/free peptide" indicates phage recovered from breast tissue when CPGPEGAGC (SEQ ID NO: 2) phage were coinjected with 0.5 ml of 2 mg/ml free corresponding peptide SEQ ID NO: 2.

Sequence analysis showed that phage displaying the heptapeptide CPGPEGAGC (SEQ ID NO: 2) were enriched among phage isolated from breast tissue, accounting for 14% of phage present in the pool. Furthermore, when tested individually, about 100 times more of the CPGPEGAGC (SEQ ID NO: 2)-displaying phage than control T7 phage homed to breast tissue. As shown in FIG. 2, the CPGPEGAGC (SEQ ID NO: 2) phage did not home to the other tissues assayed, including pancreas, brain, kidney, lung, or skin from parts of the body other than the breast fat pad. As further shown in FIG. 2, the breast-homing of the CPGPEGAGC (SEQ ID NO: 2) phage was specific; coinjection of free peptide SEQ ID NO: 2 markedly reduced phage recovery from breast tissue.

A phage display peptide library with the general structure of $CX_7C$, where C is cysteine and X is any amino acid, was constructed in T7 phage essentially as follows. Briefly, complementary oligonucleotides that encoded the random peptide insert as NNK codons, and had 5'EcoRI and 3'HindIII overhangs, were annealed. The resulting double stranded DNA was phosphorylated with T4 polynucleotide kinase (Novagen; Madison, Wis.) and ligated into 1 ug of T7Select415-1b vector arms. The ligated product was directly added to 50 µl of packaging extract and incubated for two hours, yielding $10^8$ pfu total recombinants. The recombinants were amplified in 500 ml of liquid culture. Purification of phage particles and sequencing of single stranded phage DNA was performed essentially as described in Hoffman et al., "In vivo and ex vivo selections using phage-displayed libraries" in *Phage Display: A Practical Approach*, Clarkson and Lowman, Eds. (Oxford, U.K.: Oxford University Press), 2001.

In vivo phage selection was performed as described previously with a few modifications. Briefly, mice were anesthetized with avertin and then injected intravenously with $10^9$ plaque forming units (pfu) from the $CX_7C$ library. Seven minutes after the injection, the mice were perfused through the heart with 10 ml of phosphate buffered saline (PBS). Mammary tissue was then excised, weighed, and homogenized using a Medimachine (Dako, Denmark). The resulting single cells were spun down at 1500 rpm and washed five times with PBS. Phage adherent to the cells were rescued by infecting BL21 bacteria (Novagen), and the phage quantified by plaque assay.

These results indicate that the peptide CPGPEGAGC (SEQ ID NO: 2) selectively homes to breast tissue.

EXAMPLE II

CPGPEGAGC (SEQ ID NO: 2) Phage Bind to Breast Vascular Endothelium

This example demonstrates that phage displaying the peptide CPGPEGAGC (SEQ ID NO: 2) bind the vascular endothelium of mammary tissue.

Phage overlay of tissue sections stained with the endothelial marker, CD-31, showed that the binding sites for the breast-homing phage co-localized with the endothelial marker, indicating that the CPGPEGAGC (SEQ ID NO: 2) phage primarily bound endothelial cells (FIG. 3A). Some phage binding to the parenchymal cells in breast tissue also was observed. CPGPEGAGC (SEQ ID NO: 2) phage also co-localized with CD-31 in hyperplastic mammary tissue of 45-day old MMTV PyMT mice. The vasculature of breast cancers developed by these mice, tested at 80 days of age, was also positive in the phage overlay. As further shown in FIG. 3B, phage bearing the breast homing peptide CPGPEGAGC (SEQ ID NO: 2) did not bind to vasculature of lung or liver metastases in the MMTV PyMT mice.

Phage overlay assays were performed essentially as follows. Sections from fresh frozen tissues were cut at 7 µm, air dried for one hour on microscope slides, fixed with ice-cold acetone, and air dried for 15 minutes. The slides were then incubated in 50 µl of phage solution ($10^{10}$ pfu/ml) at 4° C. for one hour; washed three times with PBS/0.01% Tween-20 (BioRad; Hercules, Calif.); and incubated with antiserum to T7 phage, followed by FITC-labeled goat anti-rabbit antibody (Molecular Probes; Eugene, Oreg.).

CD31 immunostaining was performed as follows. Sections from fresh frozen tissue were fixed as described above, and the slides incubated for one hour with monoclonal anti-CD-31 antibody (Invitrogen; La Jolla, Calif.), diluted 1/1000, followed by incubation with TRITC-labeled goat anti-mouse antibody, diluted 1/200 (Molecular Probes).

These results demonstrate that peptide CPGPEGAGC (SEQ ID NO: 2) selectively homes to the endothelium of breast tissue.

EXAMPLE III

An Aminopeptidase P-Related Clone Binds the CPGPEGAGC (SEQ ID NO: 2) Peptide

To identify the receptor for the CPGPEGAGC (SEQ ID NO: 2) peptide in breast vasculature, a breast cancer cDNA library was screened against insolubilized CPGPEGAGC (SEQ ID NO: 2) peptide. Phage recovery increased about 50-fold in 5 rounds of selection on the peptide (FIG. 4A). Among the individual phage clones from the selected pool, one clone bound avidly to the peptide-coated surface (FIG. 4B), but not to a surface treated with the blocking buffer only (not shown). As shown in FIG. 4C, sequence analysis revealed that this clone encodes a peptide that is highly homologous to the signal peptide plus the N-terminal 14 amino acids of aminopeptidase P (AmPaseP).

As shown in FIG. 5A, binding of the aminopeptidase P encoding phage to insolubilized CPGPEGAGC (SEQ ID NO: 2) peptide could be blocked by co-incubation of the phage with free peptide SEQ ID NO: 2; with apstatin (SIGMA; St. Louis, Mo.), a synthetic inhibitor of aminopeptidase P; or with an anti-aminopeptidase P antibody (Lasch et al., *Biol. Chem.* 379:705-709 (1998)). In contrast, a control antibody had no effect. Furthermore, co-injection into mice of anti-aminopeptidase P antibody with CPGPEGAGC (SEQ ID NO: 2)-bearing phage reduced by almost 90% the number of phage subsequently rescued from the breast tissue, while a control antibody did not affect breast homing of CPGPE-GAGC (SEQ ID NO: 2)-bearing phage (see FIG. 5B).

Figure 5C:
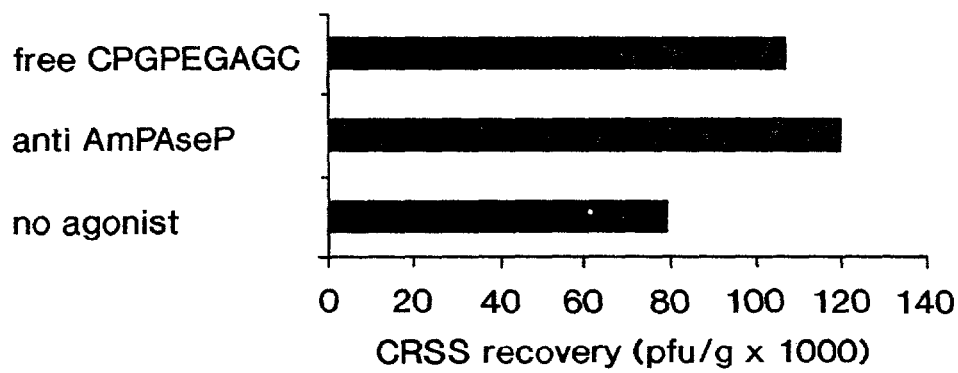

As further shown in FIG. 5C, anti-aminopeptidase P antibody did not block the breast homing of another phage, CRSS (SEQ ID NO: 2), identified in the screening for breast homing. Free CPGPEGAGC (SEQ ID NO: 2) peptide also had no effect on the recovery of the CRSS (SEQ ID NO: 3)-bearing phage from breast tissue (see FIG. 5C). These results indicate that the breast homing peptides CRSS (SEQ ID NO: 3) and CPGPEGAGC (SEQ ID NO: 2) bind distinct target receptors in breast tissue.

cDNA libraries displayed on T7 phage (Sche et al., *Chem. and Biol.* 6:707-716 (1999); Sidhu, *Curr. Opin. Biotechnol* 11:610-616 (2000); and Cochrane et al., *J. Mol. Biol.* 297:89-97 (2000)) were used to clone cDNAs encoding proteins that bound the CPGPEGAGC (SEQ ID NO: 2) peptide. The peptide was synthesized in a Symphony synthesizer (Rainin Instruments; Emeryville, Calif.), cyclized, and purified by HPLC. The peptide was immobilized on a 96 well Reacti-Bind® polystyrene strip plate (Pierce; Rockford, Ill.). The wells were then treated three times×200 µl SuperBlock® blocking buffer (Pierce).

A human breast carcinoma cDNA library on T7 phage obtained from Novagen was amplified in a single step by infecting BLT 5615 bacteria. Phage suspension (100 µl, $10^9$ pfu/ml) in PBS was incubated in the wells for one hour; the wells were then washed five times with 200 µl PBS and once with elution buffer (Novagen) to elute phage bound with low and intermediate affinity. Phage bound to the immobilized peptide were subsequently recovered by incubating BLT 5615 bacteria in the wells for 10 minutes at room temperature.

In sum, the results disclosed in this example demonstrate that aminopeptidase P is the receptor for the CPGPEGAGC (SEQ ID NO: 2) homing molecule in breast vasculature.

EXAMPLE IV

Tissue Distribution of Aminopeptidase P

This example describes the tissue distribution of aminopeptidase P.

Figure 6:
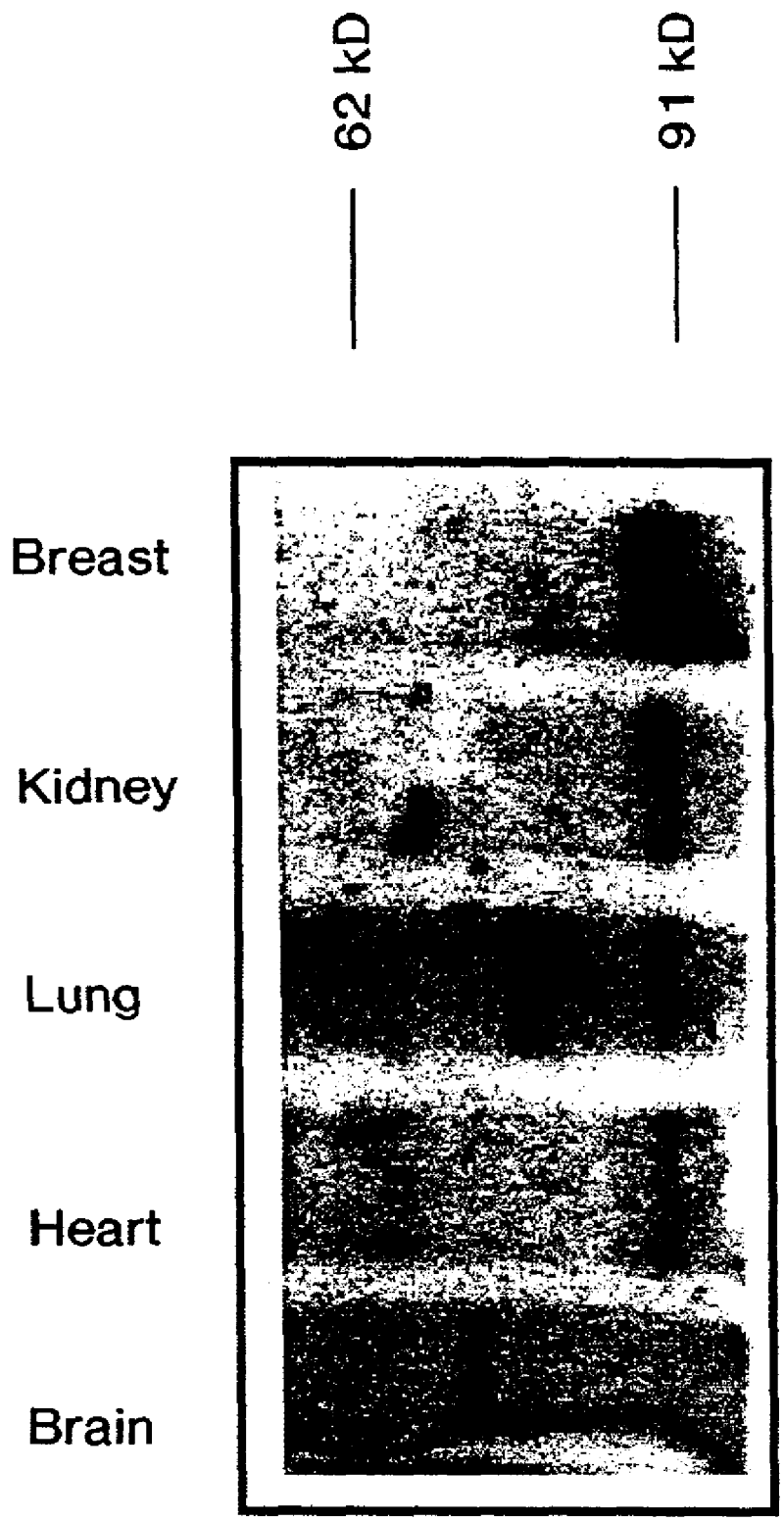
FIG. 6 shows expression of aminopeptidase P in individual mouse tissues. Lysates of various mouse tissues were tested for aminopeptidase P expression by immunoblotting with an anti-aminopeptidase P antibody.

The expression level of aminopeptidase P was determined by immunoblotting various murine tissues with anti-aminopeptidase P antibody. As shown in FIG. 6, expression of aminopeptidase P was higher in murine breast tissue than in the kidney, lung, heart or brain. Different molecular weight forms of aminopeptidase P were also observed in different organs.

Immunoblotting of aminopeptidase P was performed essentially as follows. After weighing, mouse tissues were minced with a scalpel and homogenized with a Medimachine. Cells were spun down and resuspended in lysis buffer (phosphate buffered saline, 200 mM octylglucoside, 3 mM PMSF) at 4° C. The homogenates were then passed 10 times through a 24G injection needle. Lysates were mixed with 2×sample buffer (Novex; La Jolla, Calif.), boiled for five minutes, and electrophoresed on a pre-cast 4-20% Tris-glycine SDS-PAGE gradient gel (Novex). Proteins were then electroblotted onto PVDF membranes. After blocking with TBST (Tris-buffered saline, 0.3% Tween-20) containing 20% FBS, membranes were incubated with anti-aminopeptidase P antibody diluted 1/1000 in TBST, washed 3 times with TBST, and incubated with HRP-conjugated goat anti-rabbit antibody (BioRad), diluted 1/5000 in TBST. Blots were developed by using Western Blotting Luminol Reagent from Santa Cruz Biotechnology (Santa Cruz, Calif.).

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of directing a moiety to breast vasculature in a subject, comprising administering to the subject a conjugate comprising a moiety linked to a homing molecule that selectively homes to breast vasculature, wherein said homing molecule is a peptide consisting of the amino acid sequence PGPEGAG (SEQ ID NO:1) or CPGPEGAGC (SEQ ID NO:2), whereby the moiety is directed to breast vasculature by said peptide.

2. The method of claim 1, wherein said homing molecule is a peptide consisting of the amino acid sequence PGPEGAG (SEQ ID NO:1).

3. The method of claim 1, wherein said homing molecule is a peptide consisting of the amino acid sequence CPGPEGAGC (SEQ ID NO:2).

4. The method of claim 3, wherein said homing molecule is cyclic.

5. The method of claim 1, wherein said moiety is a therapeutic agent.

6. The method of claim 1, wherein said moiety is a cancer chemotherapeutic agent.

7. The method of claim 1, wherein said moiety is a cytotoxic agent.

8. The method of claim 1, wherein said moiety is a detectable label.

9. A method of directing a moiety to breast vasculature in a subject, comprising administering to the subject a conjugate comprising a moiety linked to a homing molecule that specifically binds aminopeptidase P, wherein said homing molecule is a peptide consisting of the amino acid sequence PGPEGAG (SEQ ID NO:1) or CPGPEGAGC (SEQ ID NO:2), whereby the moiety is directed to breast vasculature by said peptide.

10. The method of claim 9, wherein said homing molecule is a peptide consisting of the amino acid sequence PGPEGAG (SEQ ID NO:1).

11. The method of claim 9, wherein said homing molecule is a peptide consisting of the amino acid sequence CPGPEGAGC (SEQ ID NO:2).

12. The method of claim 11, wherein said homing molecule is cyclic.

13. The method of claim 9, wherein said moiety is a therapeutic agent.

14. The method of claim 9, wherein said moiety is a cancer chemotherapeutic agent.

15. The method of claim 9, wherein said moiety is a cytotoxic agent.

16. The method of claim 9, wherein said moiety is a detectable label.

17. A method of imaging breast vasculature in a subject, comprising:
(a) administering to the subject a conjugate comprising a detectable label linked to a homing molecule that specifically binds aminopeptidase P, wherein said homing molecule is a peptide consisting of the amino acid sequence PGPEGAG (SEQ ID NO:1) or CPGPEGAGC (SEQ ID NO:2), whereby said peptide of said conjugate specifically binds said breast vasculature; and
(b) detecting said conjugate, thereby imaging breast vasculature.

18. The method of claim 17, wherein said homing molecule is a peptide consisting of the amino acid sequence PGPEGAG (SEQ ID NO:1).

19. The method of claim 17, wherein said homing molecule is a peptide consisting of the amino acid sequence CPGPEGAGC (SEQ ID NO:2).

20. The method of claim 19, wherein said homing molecule is cyclic.

21. The method of claim 17, wherein said detectable label is a radionuclide.

22. The method of claim 21, wherein said detectable label is selected from the group consisting of indium-111, technitium-99, carbon-11 and carbon-13.

23. A method of imaging breast vasculature in a subject, comprising:
(a) administering to the subject a conjugate comprising a detectable label linked to a homing molecule that selectively homes to breast vasculature, wherein said homing molecule is a peptide consisting of the amino acid sequence PGPEGAG (SEQ ID NO:1) or CPGPEGAGC (SEQ ID NO:2), whereby said peptide of said conjugate specifically binds said breast vasculature; and
(b) detecting said conjugate, thereby imaging breast vasculature.

24. The method of claim 23, wherein said homing molecule is a peptide consisting of the amino acid sequence PGPEGAG (SEQ ID NO:1).

25. The method of claim 23, wherein said homing molecule is a peptide consisting of the amino acid sequence CPGPEGAGC (SEQ ID NO:2).

26. The method of claim 25, wherein said homing molecule is cyclic.

27. The method of claim 23, wherein said detectable label is a radionuclide.

28. The method of claim 23, wherein said detectable label is selected from the group consisting of indium-111, technitium-99, carbon-11 and carbon-13.

* * * * *

UNITED STATES PATENT AND TRADEMARK OFFICE
CERTIFICATE OF CORRECTION

PATENT NO. : 7,666,391 B2 Page 1 of 1
APPLICATION NO. : 10/158566
DATED : February 23, 2010
INVENTOR(S) : Ruoslahti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1035 days.

Signed and Sealed this

Seventh Day of December, 2010

David J. Kappos
*Director of the United States Patent and Trademark Office*

SEQUENCE LISTING

<160> NUMBER OF SEQ ID NOS: 19

<210> SEQ ID NO 1
<211> LENGTH: 7
<212> TYPE: PRT
<213> ORGANISM: Artificial Sequence
<220> FEATURE:
<223> OTHER INFORMATION: Synthetic construct

<400> SEQUENCE: 1

Pro Gly Pro Glu Gly Ala Gly
 1               5

<210> SEQ ID NO 2
<211> LENGTH: 9
<212> TYPE: PRT

```
<213> ORGANISM: Artificial Sequence
<220> FEATURE:
<223> OTHER INFORMATION: Synthetic construct

<400> SEQUENCE: 2

Cys Pro Gly Pro Glu Gly Ala Gly Cys
  1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic construct

<400> SEQUENCE: 3

Cys Arg Ser Ser
  1

<210> SEQ ID NO 4
<211> LENGTH: 4
<212> TYPE: PRT
<213> ORGANISM: Artificial Sequence
<220> FEATURE:
<223> OTHER INFORMATION: Synthetic construct

<400> SEQUENCE: 4

Cys Arg Thr Ser
  1

<210> SEQ ID NO 5
<211> LENGTH: 36
<212> TYPE: PRT
<213> ORGANISM: Artificial Sequence
<220> FEATURE:
<223> OTHER INFORMATION: Synthetic construct

<400> SEQUENCE: 5

Met Ala Arg Ala His Trp Gly Cys Pro Trp Leu Val Leu Leu Cys Ala
  1               5                  10                  15

Cys Ala Trp Gly His Thr Lys Pro Val Asp Leu Gly Gly Gln Asp Val
                 20                  25                  30

Arg Asn Cys Ser
             35

<210> SEQ ID NO 6
<211> LENGTH: 32
<212> TYPE: PRT
<213> ORGANISM: Artificial Sequence
<220> FEATURE:
<223> OTHER INFORMATION: Synthetic construct

<400> SEQUENCE: 6

Phe Met Ala Arg Ala Ser Gly Cys Pro Leu Val Leu Arg Cys Ala Cys
  1               5                  10                  15

Asp Cys His Thr Gly Asn Val Leu Gly Gly Gln Asp Cys Asn Cys Ser
                 20                  25                  30

<210> SEQ ID NO 7
<211> LENGTH: 3431
<212> TYPE: DNA
<213> ORGANISM: Homo sapiens
<220> FEATURE:
<221> NAME/KEY: CDS
<222> LOCATION: (265)...(2286)
```

-continued

<400> SEQUENCE: 7

```
cacccctatcc tacactacta ggaacttgca cagtccgcct cgggcagccc aaagctcctc      60
tgcccaccct ggctcccaaa accctccaaa acaaaagacc agaaaagcac tctccaccca     120
gcagccaaac gcctccttct tgacgccagc cccaccctc tgtctgctcg agcccaggaa     180
aggcctgaag gaacaggccg gggaaggagc cctccctctc tcccttgtcc ctccatccac     240
ccagcgccgg catctggaga ccct atg gcc cgg gct cac tgg ggc tgc tgc        291
                             Met Ala Arg Ala His Trp Gly Cys Cys
                              1               5 ccc tgg ctg gtc ctc ctc tgt gct tgt gcc tgg ggc cac aca aag cca       339
Pro Trp Leu Val Leu Leu Cys Ala Cys Ala Trp Gly His Thr Lys Pro
 10              15                  20                  25 ctg gac ctt gga ggg cag gat gtg aga aat tgt tcc acc aac ccc cct       387
Leu Asp Leu Gly Gly Gln Asp Val Arg Asn Cys Ser Thr Asn Pro Pro
                 30                  35                  40 tac ctt cca gtt act gtg gtc aat acc aca atg tca ctc aca gcc ctc       435
Tyr Leu Pro Val Thr Val Val Asn Thr Thr Met Ser Leu Thr Ala Leu
             45                  50                  55 cgc cag cag atg cag acc cag aat ctc tca gcc tac atc atc cca ggc       483
Arg Gln Gln Met Gln Thr Gln Asn Leu Ser Ala Tyr Ile Ile Pro Gly
         60                  65                  70 aca gat gct cac atg aac gag tac atc ggc caa cat gac gag agg cgt       531
Thr Asp Ala His Met Asn Glu Tyr Ile Gly Gln His Asp Glu Arg Arg
 75                  80                  85 gcg tgg att aca ggc ttt aca ggg tct gca gga act gca gtg gtg act       579
Ala Trp Ile Thr Gly Phe Thr Gly Ser Ala Gly Thr Ala Val Val Thr
 90                  95                 100                 105 atg aag aaa gca gct gtc tgg acc gac agt cgc tac tgg act cag gct       627
Met Lys Lys Ala Ala Val Trp Thr Asp Ser Arg Tyr Trp Thr Gln Ala
                110                 115                 120 gag cgg caa atg gac tgt aat tgg gag ctc cat aag gaa gtt ggc acc       675
Glu Arg Gln Met Asp Cys Asn Trp Glu Leu His Lys Glu Val Gly Thr
            125                 130                 135 act cct att gtc acc tgg ctc ctc acc gag att ccc gct gga ggg cgt       723
Thr Pro Ile Val Thr Trp Leu Leu Thr Glu Ile Pro Ala Gly Gly Arg
        140                 145                 150 gtg ggt ttt gac ccc ttc ctc ttg tcc att gac acc tgg gag agt tat       771
Val Gly Phe Asp Pro Phe Leu Leu Ser Ile Asp Thr Trp Glu Ser Tyr
    155                 160                 165 gat ctg gcc ctc caa ggc tct aac aga cag ctg gtg tcc atc aca acc       819
Asp Leu Ala Leu Gln Gly Ser Asn Arg Gln Leu Val Ser Ile Thr Thr
170                 175                 180                 185 aat ctt gtg gac ctg gta tgg gga tca gag agg cca ccg gtt cca aat       867
Asn Leu Val Asp Leu Val Trp Gly Ser Glu Arg Pro Pro Val Pro Asn
                190                 195                 200 caa ccc att tat gcc ctg cag gag gca ttc aca ggg agc act tgg cag       915
Gln Pro Ile Tyr Ala Leu Gln Glu Ala Phe Thr Gly Ser Thr Trp Gln
            205                 210                 215 gag aaa gta tct ggc gtc cga agc cag atg cag aag cat caa aag gtc       963
Glu Lys Val Ser Gly Val Arg Ser Gln Met Gln Lys His Gln Lys Val
        220                 225                 230 ccg act gcc gtc ctt ctg tcg gcg ctt gag gag acg gcc tgg ctc ttc      1011
Pro Thr Ala Val Leu Leu Ser Ala Leu Glu Glu Thr Ala Trp Leu Phe
    235                 240                 245 aac ctt cga gcc agt gac atc ccc tat aac ccc ttc ttc tat tcc tac      1059
Asn Leu Arg Ala Ser Asp Ile Pro Tyr Asn Pro Phe Phe Tyr Ser Tyr
250                 255                 260                 265 acg ctg ctc aca gac tct tct att agg ttg ttt gca aac aag agt cgc      1107
Thr Leu Leu Thr Asp Ser Ser Ile Arg Leu Phe Ala Asn Lys Ser Arg
```

```
                Thr Leu Leu Thr Asp Ser Ser Ile Arg Leu Phe Ala Asn Lys Ser Arg
                            270                 275                 280 ttt agc tcc gaa acc ttg agc tat ctg aac tcc agt tgc aca ggc ccc            1155
Phe Ser Ser Glu Thr Leu Ser Tyr Leu Asn Ser Ser Cys Thr Gly Pro
                285                 290                 295 atg tgt gtg caa atc gag gat tac agc caa gtt cgt gac agc atc cag            1203
Met Cys Val Gln Ile Glu Asp Tyr Ser Gln Val Arg Asp Ser Ile Gln
                300                 305                 310 gcc tac tca ttg gga gat gtg agg atc tgg att ggg acc agc tat acc            1251
Ala Tyr Ser Leu Gly Asp Val Arg Ile Trp Ile Gly Thr Ser Tyr Thr
                315                 320                 325 atg tat ggg atc tat gaa atg ata cca agg gag aaa ctc gtg aca gac            1299
Met Tyr Gly Ile Tyr Glu Met Ile Pro Arg Glu Lys Leu Val Thr Asp
330                 335                 340                 345 acc tac tcc cca gtg atg atg acc aag gca gtg aag aac agc aag gag            1347
Thr Tyr Ser Pro Val Met Met Thr Lys Ala Val Lys Asn Ser Lys Glu
                350                 355                 360 cag gcc ctc ctc aag gcc agc cac gtg cgg gac gct gtg gct gtg atc            1395
Gln Ala Leu Leu Lys Ala Ser His Val Arg Asp Ala Val Ala Val Ile
                365                 370                 375 cgg tac ttg gtc tgg ctg gag aag aac gtg ccc aaa ggc aca gtg gat            1443
Arg Tyr Leu Val Trp Leu Glu Lys Asn Val Pro Lys Gly Thr Val Asp
                380                 385                 390 gag ttt tcg ggg gca gag atc gtg gac aag ttc cga gga gaa gaa cag            1491
Glu Phe Ser Gly Ala Glu Ile Val Asp Lys Phe Arg Gly Glu Glu Gln
                395                 400                 405 ttc tcc tcc gga ccc agt ttt gaa acc atc tct gct agt ggt ttg aat            1539
Phe Ser Ser Gly Pro Ser Phe Glu Thr Ile Ser Ala Ser Gly Leu Asn
410                 415                 420                 425 gct gcc ctg gcc cac tac agc ccg acc aag gag ctg aac cgc aag ctg            1587
Ala Ala Leu Ala His Tyr Ser Pro Thr Lys Glu Leu Asn Arg Lys Leu
                430                 435                 440 tcc tca gat gag atg tac ctg ctg gac tct ggg ggg cag tac tgg gac            1635
Ser Ser Asp Glu Met Tyr Leu Leu Asp Ser Gly Gly Gln Tyr Trp Asp
                445                 450                 455 ggg acc aca gac atc acc aga aca gtc cac tgg ggc acc ccc tct gcc            1683
Gly Thr Thr Asp Ile Thr Arg Thr Val His Trp Gly Thr Pro Ser Ala
                460                 465                 470 ttt cag aag gag gca tat acc cgt gtg ctg ata gga aat att gac ctg            1731
Phe Gln Lys Glu Ala Tyr Thr Arg Val Leu Ile Gly Asn Ile Asp Leu
                475                 480                 485 tcc agg ctc atc ttt ccc gct gct aca tca ggg cga atg gtg gag gcc            1779
Ser Arg Leu Ile Phe Pro Ala Ala Thr Ser Gly Arg Met Val Glu Ala
490                 495                 500                 505 ttt gcc cgc aga gcc ttg tgg gat gct ggt ctc aat tat ggt cat ggg            1827
Phe Ala Arg Arg Ala Leu Trp Asp Ala Gly Leu Asn Tyr Gly His Gly
                510                 515                 520 aca ggc cac ggc att ggc aac ttc ctg tgt gtg cat gag tgg cca gtg            1875
Thr Gly His Gly Ile Gly Asn Phe Leu Cys Val His Glu Trp Pro Val
                525                 530                 535 gga ttc cag tcc aac aac atc gct atg gcc aag ggc atg ttc act tcc            1923
Gly Phe Gln Ser Asn Asn Ile Ala Met Ala Lys Gly Met Phe Thr Ser
                540                 545                 550 att gaa cct ggt tac tat aag gat gga gaa ttt ggg atc cgt ctc gaa            1971
Ile Glu Pro Gly Tyr Tyr Lys Asp Gly Glu Phe Gly Ile Arg Leu Glu
555                 560                 565 gat gtg gct ctc gtg gta gaa gca aag acc aag tac cca ggg agc tac            2019
Asp Val Ala Leu Val Val Glu Ala Lys Thr Lys Tyr Pro Gly Ser Tyr
570                 575                 580                 585
```

```
ctg acc ttt gaa gtg gta tca ttt gtg ccc tat gac cgg aac ctc atc       2067
Leu Thr Phe Glu Val Val Ser Phe Val Pro Tyr Asp Arg Asn Leu Ile
                590                 595                 600 gat gtc agc ctg ctg tct ccc gag cat ctc cag tac ctg aat cgc tac       2115
Asp Val Ser Leu Leu Ser Pro Glu His Leu Gln Tyr Leu Asn Arg Tyr
            605                 610                 615 tac cag acc atc cgg gag aag gtg ggt cca gag ctg cag agg cgc cag       2163
Tyr Gln Thr Ile Arg Glu Lys Val Gly Pro Glu Leu Gln Arg Arg Gln
        620                 625                 630 cta cta gag gag ttc gag tgg ctt caa cag cac aca gag ccc ctg gcc       2211
Leu Leu Glu Glu Phe Glu Trp Leu Gln Gln His Thr Glu Pro Leu Ala
    635                 640                 645 gcc agg gcc cca gac acc gcc tcc tgg gcc tct gtg tta gtg gtc tcc       2259
Ala Arg Ala Pro Asp Thr Ala Ser Trp Ala Ser Val Leu Val Val Ser
650                 655                 660                 665 acc ctt gcc atc ctt ggc tgg agt gtc tagaggctcc agactctcct             2306
Thr Leu Ala Ile Leu Gly Trp Ser Val
                670 gttaaccctc catctagatg gggggctccc ttgcttagct cccctcaccc tgcactgaac     2366 ataccccaag agccctgct ggcccattgc ctagaaacct tgcattcat cctccttctc       2426 caagacctat ggagaaggtc ccaggcccca ggaaacacag ggcttcttgg ccccagatgg     2486 cacctccctg caccccgggg ttgtatacca caccctgggc ccctaatccc aggccccgaa     2546 ataggaaagc cagctagtct cttctcttct gtgatctcag taggcctaac ctataaccta     2606 acacagactg ctacagctgc tcccctcccg ccaaacaaag cccaagaaa caatgccccc      2666 taccacccaa gggtgccatg gtcccgggaa acccaacct gtcaccgcgt gttgggcgta     2726 accagaactg ttccccccca ccagggctta aaaatcgccc ccactttta accatcgtcc     2786 attaaccacc tggtgggcat agccagagct gttcgaaccc agccagggat gaaaaatcaa    2846 cccccgacat ggaacccatg attcctaaac ccgggtagg ttccatgcca agtaacagca     2906 gagggagtta agccatagga atttggctgt ggagtaagag ggaatgcggt gaggcagtgt    2966 ggaatatgac cctaccagag gttggagaac aaacttgggc agccggaacc cgtcactatt    3026 ttagattcct ggcattcgag gagccctttg aactttccaa agtgcagcca cagctacaat    3086 gctgttaaat cctcccacat ttcttggatg ccccttcacc ttgtgtggac agtgtctggt    3146 ttccccattt tacagacagg aaaactgagc ttcagacagg gggtgggctt tgcctaagga    3206 cacacaaatt tggttgggag ttgatggggc cagatgagcc agcattccag ctgtttcacc    3266 cttcagcaac atgcagagtc cctgagccca cctcccagcc ctctcctcat tctctgaacc    3326 cactgtggtg agaagaattt gctccggcca aattggccgt tagccacctg ggtccacatc    3386 ctgctaagac gtttaaaaca gcctaacaaa gacacttgcc tgtgg                    3431

<210> SEQ ID NO 8
<211> LENGTH: 674
<212> TYPE: PRT
<213> ORGANISM: Homo sapiens

<400> SEQUENCE: 8

Met Ala Arg Ala His Trp Gly Cys Cys Pro Trp Leu Val Leu Leu Cys
1               5                   10                  15

Ala Cys Ala Trp Gly His Thr Lys Pro Leu Asp Leu Gly Gly Gln Asp
            20                  25                  30

Val Arg Asn Cys Ser Thr Asn Pro Pro Tyr Leu Pro Val Thr Val Val
        35                  40                  45
```

```
Asn Thr Thr Met Ser Leu Thr Ala Leu Arg Gln Gln Met Gln Thr Gln
 50                  55                  60

Asn Leu Ser Ala Tyr Ile Ile Pro Gly Thr Asp Ala His Met Asn Glu
 65                      70                  75                  80

Tyr Ile Gly Gln His Asp Glu Arg Arg Ala Trp Ile Thr Gly Phe Thr
                 85                  90                  95

Gly Ser Ala Gly Thr Ala Val Val Thr Met Lys Lys Ala Ala Val Trp
            100                 105                 110

Thr Asp Ser Arg Tyr Trp Thr Gln Ala Glu Arg Gln Met Asp Cys Asn
                115                 120                 125

Trp Glu Leu His Lys Glu Val Gly Thr Thr Pro Ile Val Thr Trp Leu
        130                 135                 140

Leu Thr Glu Ile Pro Ala Gly Gly Arg Val Gly Phe Asp Pro Phe Leu
145                 150                 155                 160

Leu Ser Ile Asp Thr Trp Glu Ser Tyr Asp Leu Ala Leu Gln Gly Ser
                165                 170                 175

Asn Arg Gln Leu Val Ser Ile Thr Thr Asn Leu Val Asp Leu Val Trp
                180                 185                 190

Gly Ser Glu Arg Pro Pro Val Pro Asn Gln Pro Ile Tyr Ala Leu Gln
            195                 200                 205

Glu Ala Phe Thr Gly Ser Thr Trp Gln Glu Lys Val Ser Gly Val Arg
    210                 215                 220

Ser Gln Met Gln Lys His Gln Lys Val Pro Thr Ala Val Leu Leu Ser
225                 230                 235                 240

Ala Leu Glu Glu Thr Ala Trp Leu Phe Asn Leu Arg Ala Ser Asp Ile
                245                 250                 255

Pro Tyr Asn Pro Phe Phe Tyr Ser Tyr Thr Leu Leu Thr Asp Ser Ser
            260                 265                 270

Ile Arg Leu Phe Ala Asn Lys Ser Arg Phe Ser Ser Glu Thr Leu Ser
    275                 280                 285

Tyr Leu Asn Ser Ser Cys Thr Gly Pro Met Cys Val Gln Ile Glu Asp
290                 295                 300

Tyr Ser Gln Val Arg Asp Ser Ile Gln Ala Tyr Ser Leu Gly Asp Val
305                 310                 315                 320

Arg Ile Trp Ile Gly Thr Ser Tyr Thr Met Tyr Gly Ile Tyr Glu Met
                325                 330                 335

Ile Pro Arg Glu Lys Leu Val Thr Asp Thr Tyr Ser Pro Val Met Met
            340                 345                 350

Thr Lys Ala Val Lys Asn Ser Lys Glu Gln Ala Leu Leu Lys Ala Ser
        355                 360                 365

His Val Arg Asp Ala Val Ala Val Ile Arg Tyr Leu Val Trp Leu Glu
        370                 375                 380

Lys Asn Val Pro Lys Gly Thr Val Asp Glu Phe Ser Gly Ala Glu Ile
385                 390                 395                 400

Val Asp Lys Phe Arg Gly Glu Glu Gln Phe Ser Ser Gly Pro Ser Phe
                405                 410                 415

Glu Thr Ile Ser Ala Ser Gly Leu Asn Ala Ala Leu Ala His Tyr Ser
            420                 425                 430

Pro Thr Lys Glu Leu Asn Arg Lys Leu Ser Ser Asp Glu Met Tyr Leu
        435                 440                 445

Leu Asp Ser Gly Gly Gln Tyr Trp Asp Gly Thr Thr Asp Ile Thr Arg
450                 455                 460

Thr Val His Trp Gly Thr Pro Ser Ala Phe Gln Lys Glu Ala Tyr Thr
```

-continued

```
                465                 470                 475                 480
Arg Val Leu Ile Gly Asn Ile Asp Leu Ser Arg Leu Ile Phe Pro Ala
                    485                 490                 495
Ala Thr Ser Gly Arg Met Val Glu Ala Phe Ala Arg Arg Ala Leu Trp
                500                 505                 510
Asp Ala Gly Leu Asn Tyr Gly His Gly Thr Gly His Gly Ile Gly Asn
                515                 520                 525
Phe Leu Cys Val His Glu Trp Pro Val Gly Phe Gln Ser Asn Asn Ile
            530                 535                 540
Ala Met Ala Lys Gly Met Phe Thr Ser Ile Glu Pro Gly Tyr Tyr Lys
545                 550                 555                 560
Asp Gly Glu Phe Gly Ile Arg Leu Glu Asp Val Ala Leu Val Val Glu
                565                 570                 575
Ala Lys Thr Lys Tyr Pro Gly Ser Tyr Leu Thr Phe Glu Val Val Ser
                580                 585                 590
Phe Val Pro Tyr Asp Arg Asn Leu Ile Asp Val Ser Leu Leu Ser Pro
            595                 600                 605
Glu His Leu Gln Tyr Leu Asn Arg Tyr Tyr Gln Thr Ile Arg Glu Lys
        610                 615                 620
Val Gly Pro Glu Leu Gln Arg Gln Leu Leu Glu Glu Phe Glu Trp
625                 630                 635                 640
Leu Gln Gln His Thr Glu Pro Leu Ala Ala Arg Ala Pro Asp Thr Ala
                645                 650                 655
Ser Trp Ala Ser Val Leu Val Ser Thr Leu Ala Ile Leu Gly Trp
            660                 665                 670
Ser Val

<210> SEQ ID NO 9
<211> LENGTH: 5
<212> TYPE: PRT
<213> ORGANISM: Artificial Sequence
<220> FEATURE:
<223> OTHER INFORMATION: Synthetic construct

<400> SEQUENCE: 9

Cys Arg Ser Ser Asn
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic construct

<400> SEQUENCE: 10

Cys Arg Thr Ser Asn
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (6)...(7)
<223> OTHER INFORMATION: Xaa = any amino acid

<400> SEQUENCE: 11
```

Cys Arg Ser Ser Asn Xaa Xaa Cys
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (6)...(7)
<223> OTHER INFORMATION: Xaa = any amino acid

<400> SEQUENCE: 12

Cys Arg Thr Ser Asn Xaa Xaa Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic construct

<400> SEQUENCE: 13

Cys Arg Ser Ser Asn Gly Asp Cys
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic construct

<400> SEQUENCE: 14

Cys Arg Thr Ser Asn Tyr Gly Cys
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 3
<223> OTHER INFORMATION: Xaa = Thr or Ser
<220> FEATURE:
<221> NAME/KEY: VARIANT
<222> LOCATION: 6
<223> OTHER INFORMATION: Xaa = Gly or Tyr
<220> FEATURE:
<221> NAME/KEY: VARIANT
<222> LOCATION: 7
<223> OTHER INFORMATION: Xaa = Asp or Gly

<400> SEQUENCE: 15

Cys Arg Xaa Ser Asn Xaa Xaa Cys
1               5

<210> SEQ ID NO 16
<211> LENGTH: 14
<212> TYPE: PRT
<213> ORGANISM: Artificial Sequence
<220> FEATURE:
<223> OTHER INFORMATION: Synthetic construct

```
<400> SEQUENCE: 16

Lys Leu Ala Lys Leu Ala Lys Lys Leu Ala Lys Leu Ala Lys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic construct

<400> SEQUENCE: 17

Lys Leu Ala Lys Lys Leu Ala Lys Leu Ala Lys Lys Leu Ala
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic construct

<400> SEQUENCE: 18

Lys Ala Ala Lys Lys Ala Ala Lys Ala Ala Lys Lys Ala Ala
1               5                   10

<210> SEQ ID NO 19
<211> LENGTH: 21
<212> TYPE: PRT
<213> ORGANISM: Artificial Sequence
<220> FEATURE:
<223> OTHER INFORMATION: Synthetic construct

<400> SEQUENCE: 19

Lys Leu Gly Lys Lys Leu Gly Lys Leu Gly Lys Lys Leu Gly Lys Leu
1               5                   10                  15

Gly Lys Lys Leu Gly
            20
```